Figure 1:
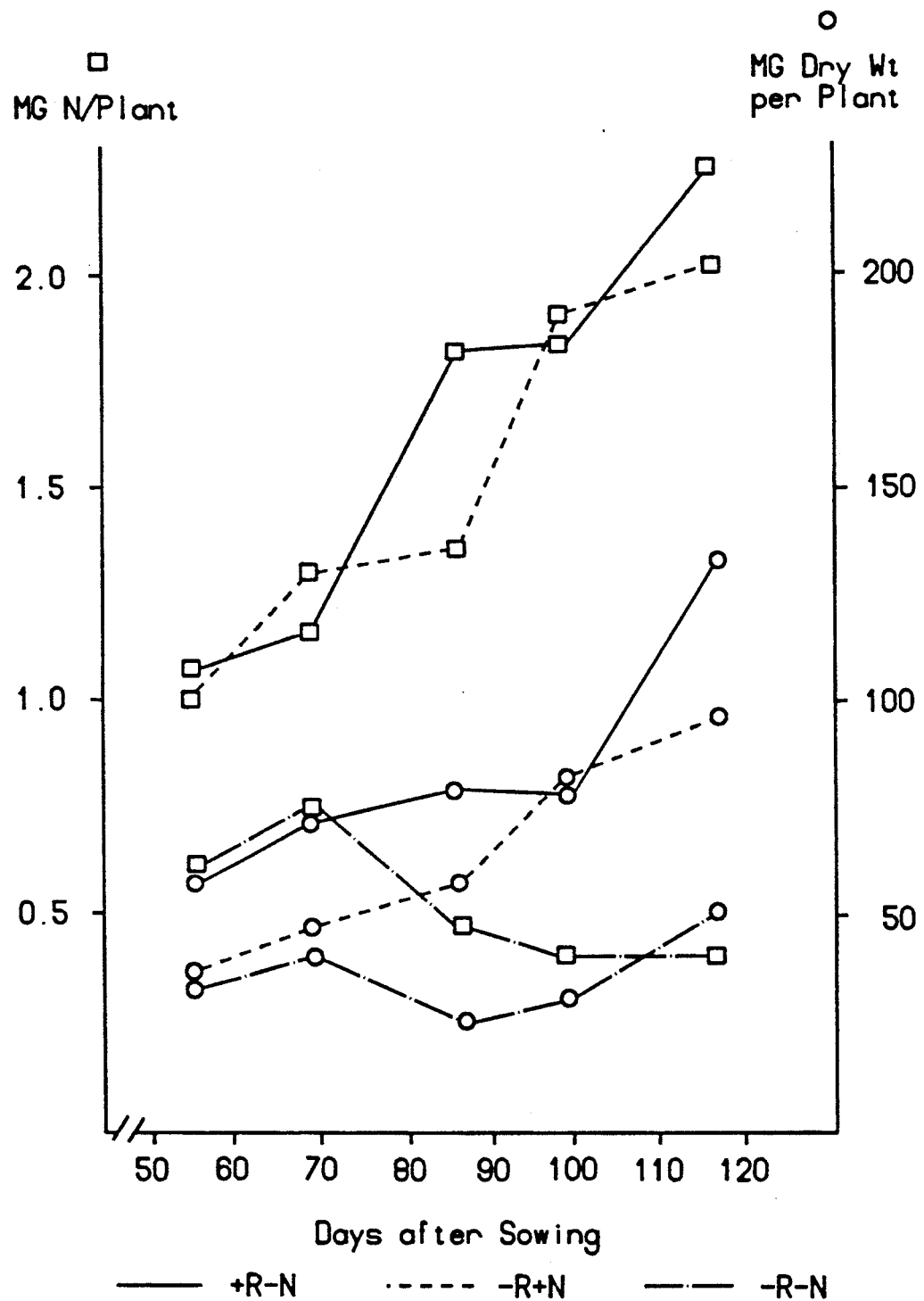

United States Patent [19]
Nielsen et al.

[11] Patent Number: 5,229,291
[45] Date of Patent: Jul. 20, 1993

[54] RHIZOBIA TRANSFORMANTS WHICH SYMBIOTICALLY FIXES NITROGEN IN NON-LEGUMES, A MATERIAL FOR TREATING SEEDS OF A NON-LEGUME PLANT, NON-LEGUME SEEDS, A NON-LEGUME PLANT AND A METHOD FOR PRODUCING RHIZOBIA TRANSCONJUNGANTS

[76] Inventors: Sven-Erik Nielsen; Grete Morch Sorensen, both of Trekanten 5, Hinnerup, Denmark, DK-8382

[21] Appl. No.: 626,233

[22] PCT Filed: Dec. 30, 1986

[86] PCT No.: PCT/DK86/00137
§ 371 Date: Sep. 28, 1987
§ 102(e) Date: Sep. 28, 1987

[87] PCT Pub. No.: WO87/04182
PCT Pub. Date: Jul. 16, 1987

Related U.S. Application Data

[63] Continuation of Ser. No. 133,107, Sep. 28, 1987, abandoned.

[30] Foreign Application Priority Data

Dec. 30, 1985 [DK] Denmark .............................. 6098/85

[51] Int. Cl.$^5$ .......................... C12R 1/41; C12Q 1/04; C12N 15/00; C12N 1/38; C05F 11/08
[52] U.S. Cl. .................... 435/252.2; 435/34; 435/172.2; 435/244; 435/252.3; 435/878; 71/7
[58] Field of Search .................. 435/34, 172.1, 172.2, 435/172.3, 244, 252.2, 252.3, 317.1, 878; 47/58; 71/7

[56] References Cited
PUBLICATIONS

Gupta et al. 1984. Indian J. Expt. Bot. 22(10): 560–563.
Marvel et al. 1985. Proc. Natl. Acad. Sci. USA 82: 5841–5845.
Plazinski et al. 1985. J. Bacteriol. 163(2): 812–815.
Child, J. 1975. Nature 253: 350–351.
Kavimandan, S. 1986. Plant Soil 96(1): 133–135.
Hess et al. 1982. Z. Pflanzenphysiol. 107(1): 81–84.
Hess et al. 1981. Z. Planzenphysiol. 101(1): 15–24.

*Primary Examiner*—David T. Fox

[57] ABSTRACT

Rhizobia transformants that nodulate and fix nitrogen in non-legumes. The nodulated non-legume plants can be grown without nitrogenous fertilizer and have at least the same or higher protein content, dry matter content and nitrogen content than their non-nodulated counterparts which are fertilized by the addition of nitrogenous fertilizer. The straw remaining after harvesting the nodulated non-legumes is also high in protein content.

16 Claims, 2 Drawing Sheets

RHIZOBIA TRANSFORMANTS WHICH SYMBIOTICALLY FIXES NITROGEN IN NON-LEGUMES, A MATERIAL FOR TREATING SEEDS OF A NON-LEGUME PLANT, NON-LEGUME SEEDS, A NON-LEGUME PLANT AND A METHOD FOR PRODUCING RHIZOBIA TRANSCONJUNGANTS

This is a continuation of application Ser. No. 07/133,107, filed Sep. 28, 1987, now abandoned.

TABLE OF CONTENTS

1. Field of the Invention
2. Background of the Invention
2.1. Biological Nitrogen Fixation
   2.1.1. Legume Genes Involved in Symbiosis
   2.1.2. Rhizobium Genes Involved in Symbiosis
   2.1.3. Biological Nitrogen Fixation and Non-Legumes
3. SUMMARY OF THE INVENTION
3.1. Definitions
4. Brief Description of the Figures
5. Detailed Description of the Invention
5.1. The Rhizobia Transformants
   5.1.1. Nutrient Media for Identification of Rhizobia Transformants
   5.1.2. The Alternating Line Culture Method for Producing Rhizobia Transconjugants
   5.1.3. Alternate Methods for Producing Rhizobia Transformants
5.2. Non-Legume Seed Coatings and Coated Seeds
   5.2.1. The Non-Legume Seed Coating
   5.2.2. Methods for Coating the Non-Legume Seeds
5.3. Establishing Symbiotic Nitrogen Fixation in the Non-Legumes
5.4. The Nodulated Non-Legumes
   5.4.1. Nodule Characteristics
6. Example: Materials and Methods for the Production of Rhizobia Transconjugants and Nodulation of Non-Legumes
6.1. The Alternating Line Culture Method
   6.1.1. Isolation of Parent Rhizobia
   6.1.2. Nutrient Agar Medium
   6.1.3. Legume Plant Extract
   6.1.4. Isolation of the Rhizobia Transconjugants
6.2. Preparation of the Non-Legume Seeds
6.3. Infection of Non-Legumes with Rhizobia $F_2$ Transconjugants
   6.3.1. Laboratory Studies
   6.3.2. Field Studies
6.4. Protocol for Analysis of Dry Mass, Nitrogen Content and Protein Content of Nodulated Non-Legumes
7. Example:*Rhizobium tritici* which Nodulates Wheat
7.1. Preparation of *Rhizobium tritici*
7.2. Nodulation of Wheat with *Rhizobium tritici*
   7.2.1. Laboratory Study
   7.2.2. Field Study
7.3. Analysis of Dry Mass, Nitrogen Content and Protein Content of Nodulated Wheat
   7.3.1. Results of Laboratory Study
   7.3.2. Results of Field Study
8. Example:*Rhizobium hordei* which Nodulates Barley
8.1. Preparation of *Rhizobium hordei*
   8.1.1. Characterization of *Rhizobium hordei*
8.2. Nodulation of Barley with *Rhizobium hordei*
   8.2.1. Laboratory Study
8.3. Analysis of Dry Mass, Nitrogen Content and Protein Content of Nodulated Barley
   8.3.1. Results of Laboratory Study
8.4. $^{15}N$ Enrichment in Nodulated Barley
8.5. Morphology of the Nodules
8.6. Antibiotic Resistance of Reisolated Barley Bacteroids
9. Example:*Rhizobium sorghi* which Nodulates Sorghum
9.1. Preparation of *Rhizobium sorghi*
9.2. Nodulation of Sorghum with *Rhizobium sorghi*
   9.2.1. Laboratory Study
   9.2.2. Field Study
9.3. Analysis of Nitrogen Content and Protein Content of Nodulated Sorghum
   9.3.1. Results of Laboratory Study
   9.3.2. Results of Field Study
10. Example:*Rhizobium oryzae* Which Nodulates Rice
10.1. Preparation of *Rhizobium oryzae*
10.2. Nodulation of Rice With *Rhizobium oryzae*
   10.2.1. Field Study
10.3. Analysis of Protein and Nitrogen Content of the Nodulated Rice
   10.3.1. Results of Field Study
11. Example:*Rhizobium* as a Nitrogen Fertilizer for Eucalyptus
11.1. Preparation of *Rhizobium eul*
11.2. Treatment of Eucalyptus with *Rhizobium eul*
12. Example:*Rhizobium Rl* Which Nodulates Brassicas
12.1. Preparation of *Rhizobium Rl*
12.2. Treatment of Rape with *Rhizobium Rl*
13. Example: Total Nitrogen Analysis of Nodulated Non-Legumes
13.1. Materials and Methods
13.2. Wheat and Barley
13.3. Shorghum and Rice
13.4. Rape
14. Deposit of Microorganisms

1. FIELD OF THE INVENTION

The present invention discloses Rhizobia transformants that infect, nodulate and fix nitrogen in non-legume plants grown from seeds coated with a material specific for the Rhizobia transformant. The nodulated non-legumes can be grown without using nitrogenous fertilizer; plants and the straw remaining after harvest have a higher protein content, dry matter content and nitrogen content than their non-nodulated counterparts.

The invention is illustrated by way of specific examples in which Rhizobia transconjugants ar used to nodulate grasses (the Poaceae family) including wheat, barley, sorghum, rice and Brassicas (the Cruciferae family) such as rape. Rhizobia transconjugants which fix nitrogen in eucalyptus (the Myrtaceae family) are also illustrated in the examples.

2. BACKGROUND OF THE INVENTION

An essential aspect of plant metabolism is the use of nitrates and other inorganic nitrogen compounds in the synthesis of organic compounds such as amino acids, proteins, chlorophylls, vitamins, hormones and alkaloids which are essential to plant growth and development. Although plants absorb nitrates and other nitrogen compounds from the soil, the ultimate source of nitrogen is the free dinitrogen ($N_2$) of the atmosphere;

however, free dinitrogen as such, must be fixed and converted to a form that can be utilized by the plant.

2.1. BIOLOGICAL NITROGEN FIXATION

Biological dinitrogen fixation (more commonly referred to as biological nitrogen fixation) is a complicated process involving the stepwise reduction of free nitrogen to ammonia through a series of intermediates; it is accomplished by nitrogen-fixing microorganisms some genera of which live symbiotically with certain vascular plants. The most important genus of the symbiotic nitrogen-fixing bacteria is Rhizobium, which has numerous species, each of which is symbiotic with one or a few closely related species of legume plants (e.g., peas, beans, clovers, etc). As a result, legumes, unlike other plants which are unable to fix nitrogen, do not require nitrogenous fertilizers for growth; in fact, legumes can enrich the nitrogen content of the soil. In view of the economic importance of many legumes, bacterial cultures are available for inoculating legume seeds; in addition, legume seed coatings containing viable rhizobia have been disclosed (U.S. Pat. No. 3,499,748 and U.S. Pat. No. 4,149,869).

Symbiotic nitrogen fixation involves the following: a Rhizobium bacterium which is specific for a particular legume host infects the root of the legume host. Thereafter a nodule develops on the root in which the Rhizobia live in an endosymbiotic state known as bacteroids which perform unique functions, such as nitrogen fixation, in close cooperation with the legume host; the bacteroid behaves almost like an organelle. Interestingly, Rhizobia do not generally fix nitrogen ex planta. For a review of various aspects of biological nitrogen fixation in legumes, see Chapters 3, 4, and 5 in "Plant Gene Research—Genes Involved in Microbe Plant Interactions", D. P. S. Verma, T. H. Hohn, Springer-Verlag, N.Y., 1984.

Infection, nodulation and nitrogen fixation each involve an intricate interaction between the Rhizobium and its specific legume host. In order for the initial infection to occur, the Rhizobium and the legume plant must "recognize" each other. This very specific recognition is believed to involve an interaction between a lectin of the legume host (a glycoprotein found on the root hairs) and polysaccharides on the bacterial surface; this interaction can be regarded as a very specific "lock and key" type of mechanism, the specificity of which has been compared to an antibody-antigen interaction, without which, infection cannot occur. Following the specific recognition and attachment of Rhizobium to the root of a particular legume host, infection of the host proceeds in a non-pathogenic fashion controlled by the host responses to the invading Rhizobia. Generally, the Rhizobia enter the legume through the root hairs and bacterial invasion is mediated by a tubular structure formed by the host plant called the infection thread, which invades the inner cells of the root cortex. The Rhizobia are released from the infection thread but remain enclosed in a host derived membrane envelope called the peribacteroid membrane; thus the bacteroids are restricted to extracellular compartments. Disruption of this delicate sequence of events could lead to infection that is pathogenic to the host.

After infection of the host legume by the Rhizobium, subsequent nodulation occurs only in response to an intricate interplay of events in which the legume influences the expression of Rhizobium genes and the Rhizobium, in turn, influences activity of the legume genes required for nodulation. The cells in the nodule tissue are highly organized in zones that have plant-specific arrangements; the bacteria are routinely found in the peribacteroid membranes which exclude the bacteria from the epidermal and meristematic zones. The organization and morphology of the nodule is significant biochemically in that problems of diffusion must be solved in order to provide for entry of oxygen and nutrients for the bacteroids and exit of ammonia for the host plant. A distinctive feature of effective root nodules, i.e., nodules which actually fix nitrogen, is the presence of leghemoglobin, an oxygen binding protein which appears to be involved in nodule respiration (i.e., the high concentration of this protein facilitates diffusion of oxygen into the bacteroid domains) and in the protection of nitrogenase (an enzyme essential in the nitrogen fixation pathway) from being poisoned by excess oxygen. Leghemoglogin is apparently a truly symbiotic product—the globin proteins are coded by plant genes and the haem synthesis is contributed by the bacteria Ultimately, symbiotic nitrogen fixation which occurs in the nodule is a joint endeavor The bacteroids contain the machinery for nitrogen fixation and the legume partner assimilates the ammonia produced into an organic form which is then used for the nutrition of the whole plant and the bacteroids; the legume partner provides a suitable environment and a source of energy that enables the bacteroids to fix nitrogen. Much can go wrong with the entire process: if the host plant bacteria are "mismatched" infection will not be successful, thus the whole process of nodulation and symbiotic nitrogen fixation will not occur. Moreover, successful nodulation does not mean that nitrogen fixation will necessarily occur because the resulting nodule could be defective.

2.1.1. LEGUME GENES INVOLVED IN SYMBIOSIS

Two major groups of host gene products, leghemoglobins and nodulins, are induced specifically during symbiotic nitrogen fixation. While the structure and function of leghemoglobin in the nodules is relatively clear, little is known about the nodulins. Interestingly, a recent article reported that leghemoglobin plant DNA sequences were detectable in non-legumes, thus suggesting that the genes for these oxygen-binding proteins may be more widely dispersed than previously thought (Hattori & Johnson, 1985, Plant Mol. Biol 4:285–292).

2.1.2. RHIZOBIUM GENES INVOLVED IN SYMBIOSIS

A few years ago it was discovered that Rhizobial enes needed for nodulation (nod) are located on a large plasmid (called the symbiosis plasmid) which also carries the nitrogen fixation (nif) genes themselves. It has since been found that many of the Rhizobia bacteria could be induced to recognize a new legume partner by transferring into that rhizobium a symbiosis plasmid from another species of rhizobium having a different host specificity. There is no indication that transfer of Rhizobium symbiosis plasmids from one Rhizobium to another could expand the host range to non-legumes. Interestingly, the introduction of a rhizobial symbiosis plasmid into *Agrobacterium tumefaciens* (a bacteria which causes tumorous plant growth called crown galls) confers on the Agrobacterium the ability to produce root nodules in legumes; however the nodules are defective in that they do not fix nitroqen (Hooykaas, In "Molecular Genetics of the Bacteria-Plant Interaction", A. Puhler, eds, Springer-Verlag, NY, 1983, pp.229-239).

Over the years a variety of evidence has shown that nodulation efficiency of Rhizobia bacteria in legumes is increased by exposure to certain plant exudates; perhaps this exposure stimulates expression of the nod gene. All legume root exudates produce this effect, but exudates from a variety of non-legumes do not.

2.1.3. BIOLOGICAL NITROGEN FIXATION AND NON-LEGUMES

A non-rhizobium genus of bacteria called Frankia is symbiotic with some vascular non-legume plants such as Alnus (alder), Casuarina (cassowary tree), Ceanothus, Eleagnus, Myrica (myrtle) and Psychotria (a tropical woody plant). A report based upon data derived from in vitro associations of a tobacco cell culture system and rhizobia, indicates that some non-legumes may provide factors that can be utilized by Rhizobia (Gibson et al., 1976, Planta 128: 233-239); however, no specific recognition, symbiotic relationship or specific interactions were indicated or observed. In fact, the only known example, outside the legume order, of a stable symbiosis between a non-legume seed plant and Rhizobium is that of Parasponia, a tropical large Malayan (elm) family; naturally occurring Rhizobium strains isolated in Australia were found to nodulate and fix nitrogen in Parasponia (Trinick, 1980, New Phytol. 85:37-45 and 86: 17-26; Trinick, 1981, Current Perspectives in Nitrogen Fixation, Gibson et al., eds. Elsevier Press, p.480; Trinick et al., 1976, Arch. Microbiol. 108:159-166; see also Bender et al., 1985, Plant Science 38:138-140).

3. SUMMARY OF THE INVENTION

Rhizobia transformants are described which can symbiotically fix nitrogen in non-legumes. More specifically, the Rhizobium transformants of the present invention can (a) infect the roots of non-legume plants derived from seeds coated with a protein mixture specific for the Rhizobium transformant: (b) nodulate the roots of these non-legume plants: and (c) fix nitrogen in the nodules thus eliminating the requirement of using nitrogen fertilizer to promote plant growth and development in these non-legumes. A nutrient media is described which is useful in the identification of various Rhizobia species and the transformants of the present invention.

Coated non-legume seeds are also described which, in part, allow for the establishment of symbiotic nitrogen fixation in non-legumes by the Rhizobia transformants of the present invention. These seed coatings comprise legume extracts, chromatographic fractions of legume extracts, crystals or purified proteins which are specific for the Rhizobium transformant. The seed coating may also include the Rhizobium transformant itself as an ingredient.

Methods are described for producing Rhizobium transformants, coating the non-legume seeds and for establishing symbiosis between the Rhizobium transformants and the non-legume.

3 1. DEFINITIONS

As used herein, the term "Rhizobium transformant" is defined as a Rhizobium containing introduced DNA which may be produced by any of a number of methods, including but not limited to transformation (i.e., infection with plasmid DNA), transfection (i.e., infection with free DNA, phage DNA, or viral DNA), or conjugation (i.e., the transfer of a replica plasmid from one bacterium to another); the bacterial transformants resulting from conjugation are a subset of the transformants of the present invention and may be specifically referred to as transconjugants.

The term "parent Rhizobia", as used herein, is defined as the parent species which are conjugated to produce Rhizobium transconjugants of the present invention, as well as the Rhizobia species from which plasmids or DNA sequences can be isolated and used to transform Rhizobia to produce the Rhizobium transformants of the present invention.

4. BRIEF DESCRIPTION OF THE FIGURES

FIG. 1 is a graph that represents the dry matter content (A) and nitrogen content (B) of wheat plants harvested at various times after planting. Three groups of wheat are represented: wheat nodulated by Rhizobium transconjugants ($+R-N$); wheat fertilized with a nitrogenous fertilizer but not treated with Rhizobium transconjugants ($-R+N$); and wheat neither nodulated by Rhizobium transconjugants nor treated with nitrogenous fertilizer ($-R-N$).

Figure 2:
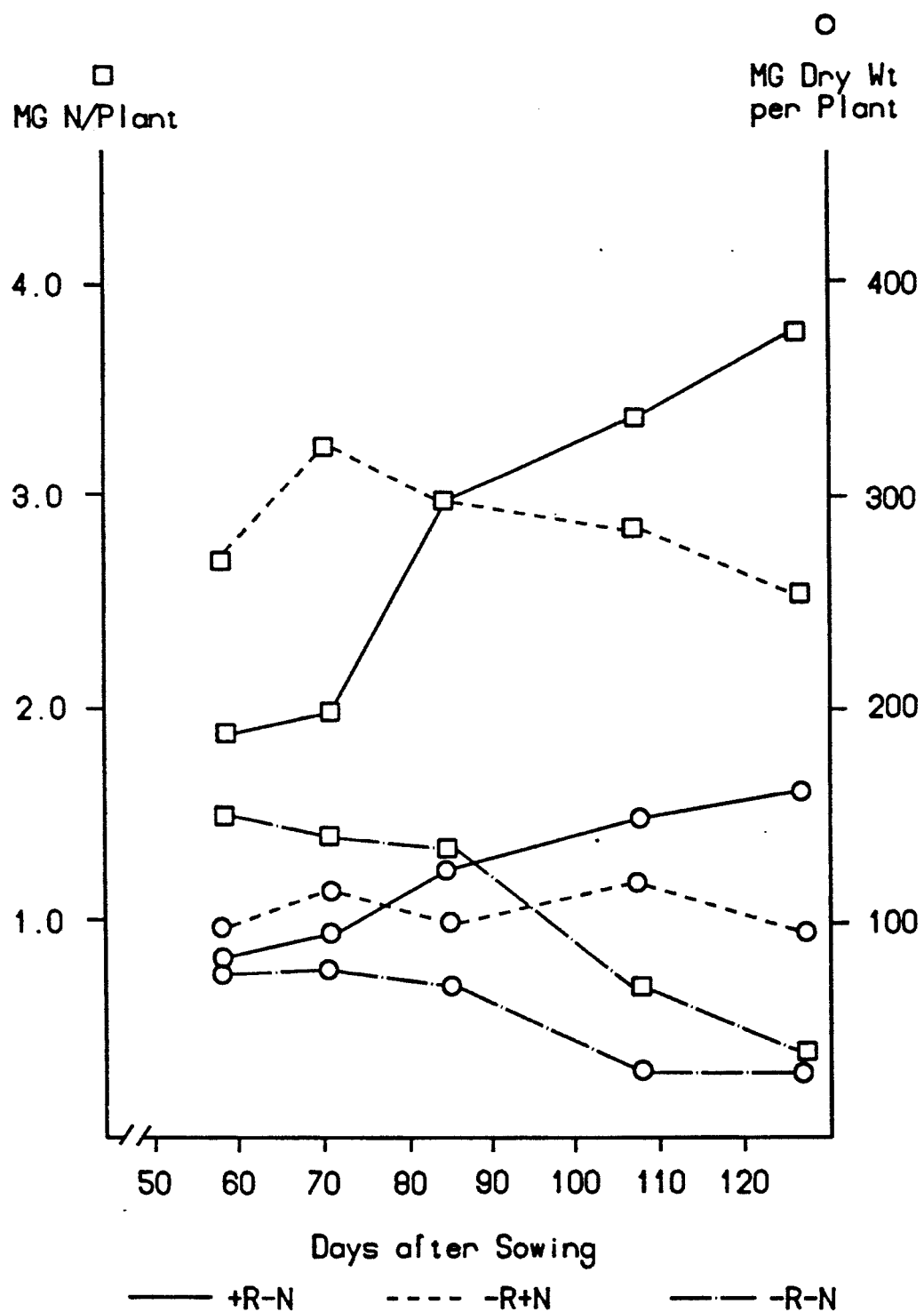

FIG. 2 is a graph that represents the dry matter content (A) and nitrogen content (B) of barley plants harvested at various times after planting. Three groups of barley are represented: barley nodulated by Rhizobium transconjugants ($+R-N$); barley fertilized with a nitrogenous fertilizer but not treated with Rhizobium transconjugants ($-R+N$); and barley neither nodulated by Rhizobium transconjugants nor treated with nitrogenous fertilizer ($-R-N$).

5. DETAILED DESCRIPTION OF THE INVENTION

The present invention is directed to Rhizobia transformants that nodulate and fix nitrogen in non-legumes. The nodulated non-legume plants can be grown without nitrogenous fertilizer and have the same or higher protein content, dry matter content and nitrogen content than their non-nodulated counterparts which are fertilized by the addition of nitrogenous fertilizer. The straw remaining after harvesting the nodulated non-legumes is also high in protein content.

More specifically, the Rhizobia transformants of the present invention are capable of nodulating non-legume plants grown from seeds coated with a material specific for the particular transformant. The invention is directed to the Rhizobia transformants, methods for producing the Rhizobia transformants, the material used to coat the non-legume seeds, the coated seeds themselves, methods for nodulating the non-legume plants with the Rhizobia transformants, and the resulting nodulated non-legumes which have a high protein content.

For purposes of clarity of description, the invention is discussed in the subsections below in the following order: (a) the Rhizobium transformants; (b) the non-legume seed coatings; (c) establishing symbiotic nitrogen fixation in the non-legume: and (d) the nodulated non-legumes.

5.1. THE RHIZOBIA TRANSFORMANTS

The production and identification of the Rhizobia transformants of the present invention was based upon the initial discovery that each different species of Rhizobia, when grown outside its legume host on nutrient medium produces a colony having a particular color, provided the nutrient medium contains, in addition to the nutrients necessary to support bacterial growth, a non-denatured extract derived from the legume host which is the specific partner of the Rhizobium species. The colony color can be utilized as a means to identify the particular Rhizobium species. In fact, different species of Rhizobia can be cultured on a nutrient medium which contains a mixture of the non-denatured extracts of each legume host specific for each species; each species will form colonies having its characteristic color.

The present invention is also based upon the further discovery that the Rhizobia transformants which can infect, nodulate and fix nitrogen in non-legumes form snowy white colonies on nutrient media which contains extracts of the legume host partners of the parent Rhizobia of the transformant; and that the transformant bacteroids which are isolated from the non-legume root nodule and cultured on the medium defined above which contains, in addition, an extract of the non-legume host, will form colonies that are greyish in color. Thus, the nutrient media provide a relatively uncomplicated means for identifying the transformants of the present invention. The nutrient media are described in the subsection below.

5.1.1. NUTRIENT MEDIA FOR IDENTIFICATION OF RHIZOBIA TRANSFORMANTS

The nutrient medium should contain the nutrients necessary for growth of the Rhizobium, including but not limited to any of the well known sources of carbon, nitrogen, and salts as well as vitamins of the B-group and the essential amino acids such as L-alanine, L-serine and L-tryptophan which can be present in the form of individual amino acids, tripeptides or oligopeptides, etc. The legume extract ingredient is useful for the identification of Rhizobia species but is not necessary for the nutrition of the Rhizobia; i.e., if a Rhizobium is grown on a nutrient medium that either does not contain its legume host extract or contains denatured legume host extract (e.g., autoclaving the media after the addition of the legume extract denatures the extract) colonies will be formed but the colony of each Rhizobium species will be clear in color. Table I below lists the characteristic colony colors formed by the various Rhizobia species grown on nutrient medium containing the extract of the legume host partner of each species streaked on the plate. It should be noted that incubation of the medium used in the examples of the present invention at a temperature above 32° C. will result in the formation of red colonies by all Rhizobia colonies growing on the medium; this is a reversible color change in that the characteristic color of each colony will return when the temperature is lowered, for example to somewhere between 18° C. and 30° C. Additionally, the nutrient medium can be altered, by the addition of cystein and phenylalanine, to produce colonies having different shades of the characteristic color for that species.

TABLE I

COLONY COLOR OF DIFFERENT RHIZOBIA SPECIES GROWN ON NUTRIENT MEDIUM CONTAINING EXTRACT OF THE HOST SPECIFIC LEGUME PARTNER*

| Rhizobium | Legume Host Partner | Colony Color |
| --- | --- | --- |
| R. cowpea | Vigna (Peanut, Mimosa Acacia, Leucaena) | greyish brown |
| R. japonicum | Glycin (Soybean) | reddish orange |
| R. leguminosarum | Lathyrus (Pea) | golden yellow |

TABLE I-continued

COLONY COLOR OF DIFFERENT RHIZOBIA SPECIES GROWN ON NUTRIENT MEDIUM CONTAINING EXTRACT OF THE HOST SPECIFIC LEGUME PARTNER*

| Rhizobium | Legume Host Partner | Colony Color |
| --- | --- | --- |
| R. lupini | Lupinus (Lupine) | light yellow |
| R. meliloti | Melilotus (Sweet Clover) | yellowish brown |
| R. phaseoli | Phaseolus (Bean) | dark brown |
| R. trifoli | Trifolium (Clover) | light brown |

*Colonies are incubated at a temperature below 32° C. (e.g., between 18° C. and 30° C.) on the nutrient medium described in more detail in Section 6.1.

The legume extracts used in the nutrient medium may be produced from any part of the legume host plant, including but not limited to shoots, stems, roots or seeds; the extracts of young shoots appear to result in the fastest color reaction. The legume extracts can be prepared by dividing the plant part into fine particles, homogenizing the macerated material in ethanol with a buffer at a pH of about 7.2 and pelleting the insoluble material by centrifugation. The supernatant can be dialyzed against distilled water until it is clear whereupon it may be again centrifuged. The entire process is carried out at 4° C. to minimize decomposition of the plant substances.

The legume extract can be fractionated chromatographically according to a method which is a modification of Allen et al., 1973, Biochem. J. 131: 155–162; Allen et al., February 1975, FEBS Letters 50(3): 362–364; Gordon et al., August 1972 FEBS Letters 24(2): 193–196; Peomans et al., 1982, Planta 156: 568–572; and Trowbridge, 1974, J. Biol. Chem. 249: 6004–6012. Briefly, this involves the chromatographic separation of the extract using a column of galactose-derivatized CH-Sepharose 4B (Pharmacia, Sweden) and DEAE-52 (Whatman) as follows: (a) the extract is first applied to the galactose derivatized CH-Sepharose 4B column. Unbound substances are removed and saved by washing the column with buffer and collecting 5 ml fractions which are assayed spectrophotometrically by absorbance at a wavelength of 280 μm; the wash is continued until no significant absorbance is detected in the effluent. The fractions which demonstrate absorbance at 280 nm are pooled and saved for chromatography on DEAE-52. The substances which bound to the galactose-derivatized Sepharose 4B column bed are eluted by the addition of 4% glucose to the column; the eluent is collected in 5 ml fractions which are also assayed by absorbance at 280 nm; (b) the fractions containing the substances which did not bind to the galactose derivatized Sepharose 4B are applied to a DEAE-52 column, which is first eluted at pH 7.2 and then at pH 9.2; five ml fractions are collected and assayed for absorbance at 280 nm. The fractions comprising the peak absorbance value at pH 7.2 are pooled and those comprising a peak absorbance value at pH 9.2 are pooled. These three fractions of a particular legume host (i.e., the fraction eluted using glucose and the fractions eluted at pH 7.2 and p 9.2) can be combined and used in place of the whole extract in the nutrient media described above. In fact, the active component of the three fractions can be crystallized and stored. These crystals derived from the legume host can be used in place of the legume host extract as an ingredient in the nutrient media used to identify the Rhizobia transformants of the present invention.

Although we are not bound to any theory or explanation of the invention, the chromatographic fractions probably contain protein, and possibly glycoproteins. The affinity to the derivatized Sepharose 4B suggests that it is likely that at least one of the proteins is a lectin. This could be significant since legume lectins are thought to be important in the initial recognition of Rhizobium partners. Once the amino acid sequences of these proteins are determined, these proteins can be made by chemical synthetic methods or via recombinant DNA techniques, using prokaryotic or eukaryotic host-vector expression systems to express the proteins. Expression of the protein in a eukaryotic host-vector expression system may be preferred because the eukaryote can process the protein in a manner that is more similar to the naturally occurring proteins. This could be especially important if the protein is a lectin. In addition, the identified proteins may be isolated from sources other than the legume host. We do not, by this theory, exclude the possiblity that other factors present in the extract such as carbohydrates, alkaloids, hormones, etc. could be a significant factor in the activity of the extract.

Although the nutrient media described above afford a convenient assay for identifyinq the transformants of the present invention, a preliminary characterization of the transformant DNA has been undertaken. The Rhizobia transformants of the present invention which symbioticially fix nitrogen in non-legumes appear to possess plasmids that are not contained in the parent Rhizobia of the transconjugant. While we are not bound to any theory or explanation of the invention, it is interesting to note that these plasmids could contain the DNA sequences responsible for the new host range of the Rhizobium transformants.

Methods for producing the Rhizobia transformants of the present invention are discussed in more detail below.

5.1.2. THE ALTERNATING LINE CULTURE METHOD FOR PRODUCING RHIZOBIA TRANSCONJUGANTS

The alternating line culture method for producing Rhizobium transconjugants of the present invention involves the following: two different Rhizobia species (the parent generation) are streaked in alternating rows on a solid nutrient medium containing in addition to the nutrients essential for bacterial growth either: (a) a mixture of non-denatured extracts of the legume host partners of each Rhizobia species; (b) the three chromatographic fractions obtained from the extract of each legume host as described in section 5.1.1. above; (c) the crystals obtained from the chromatographic fractions of each legume host; or (d) proteins (indluding glycoproteins) related thereto. Hereinafter these components will be referred to as the legume extract, chromatographic fractions, crystals, or proteins. Each parent Rhizobium species will form colonies having a characteristic color along the streak. Rhizobia transconjugants (herein called the Rhizobia $F_1$ transconjugants) are produced in between the alternating rows of parent colonies. The Rhizobia $F_1$ transconjugants, unlike their parents, form milky white colonies and cannot nodulate any plant.

The Rhizobia $F_1$ transconjugants are isolated from the milky white colonies and cultured in alternating rows with a third parent Rhizobium species on solid nutrient medium containing in addition to the legume extracts, chromatographic fractions, crystals or proteins used to produce the $F_1$ transconjugant, a third non-denatured legume extract, chromatographic fractions, crystals or proteins derived from the legume host partner of the third parent Rhizobium species. Rhizobium $F_2$ transconjugants are produced in between the alternating rows of the milky white colonies formed by the Rhizobium $F_1$ transconjugant and the colored colonies formed by the third parent Rhizobium. The Rhizobium $F_2$ transconjugant colonies are identified by their snowy white color and are able to infect, nodulate and fix nitrogen in non-legumes grown from seeds which are treated and sown as described herein.

The identification and selection of Rhizobium $F_1$ and $F_2$ transconjugants produced above is made possible because of the specilized media used. When each cross is performed, two kinds of colonies develop in between the rows of parents: (a) colonies which have a color comprising a mixture of the colors of the parent colonies and (b) the milky white $F_1$ transconjugant colonies or the snowy white $F_2$ transconjugant colonies. The mixed colored colonies comprise Rhizobia which are not stable; these Rhizobia can nodulate the legume host partners of both parent Rhizobia, however, only in one generation. In other words, the bacteroids recovered from the nodules of each legume host can only nodulate that particular legume host again. The $F_1$ transconjugants of the milky white colonies are stable but are incapable of nodulating any plant. Surprisingly, the $F_2$ transconjugants of the snowy white colonies are stable Rhizobia which can nodulate and symbiotically fix nitrogen in non-legumes.

The parent Rhizobia used to produce the $F_2$ transconjugants can comprise a third species of Rhizobia, another $F_1$ transconjugant or possibly another $F_2$ transconjugant. If the third parent comprises another $F_1$ transconjugant, then the nutrient media will contain at least four legume extracts, chromatographic fractions, crystals or proteins; i.e., those of the legume host partner for each of the two parent Rhizobia used to produce each of the two $F_1$ transconjugants. If the third parent comprises an $F_2$ transconjugant, then the nutrient media will contain at least five host legume extracts, chromatographic fractions, crystals, or proteins; i.e., those of the legume host partner for each of the two parent Rhizobia used to produce the $F_1$ transconjugant as well as the legume host partner for each of the three parent Rhizobia used to produce the $F_2$ transconjugant.

The alternating rows of parent colonies is a convenient approach for producing the transconjugants; however, any pattern or method of inoculation may be used to grow the parent colonies in proximity to one another so that conjugation can occur. Thus circles, ellipses, wavy or spiral patterns may be used. In fact, a number of different parents can be streaked on the plates to produce a number of different transconjugants on the same plate.

5.1.3. ALTERNATE METHODS FOR PRODUCING RHIZOBIA TRANSFORMANTS

Although the alternating line culture method is a convenient way to produce Rhizobium $F_2$ transformants the present invention is not limited to this method. In fact, in addition to conjugation, transformation with the appropriate plasmid responsible for the increased host range specificity of the rhizobirum is contemplated as being within the scope of the present invention. In addition, recombinant DNA techniques, including the use of phages and other vectors for infection of Rhizobia with the appropriate sequences is contemplated as within the scope of the present invention.

For example, a particularly useful system for Rhizobia is the Tn5 transposon which can be used in a scheme to transform Rhizobia. Symbiosis plasmids (Sym plasmids) can be identified by hybridization with a labeled DNA probe containing nif genes. Transfer of this sym plasmid can be accomplished by using Tn5 to incorporate (a) a marker gene into the sym plasmid, e.g., a gene for antibiotic resistance can be incorporated into the sym plasmid using transposon Tn5 by a conjugating donor and recipient bacteria and selecting hybrids based upon the acquired resistance; (b) by cloning the sym plasmid or portions thereof in *E. coli* and transforming Rhizobia with the plasmid itself; (c) by recombining the plasmid with transport genes together with the marker gene (e.q., antibiotic resistance) such as $p^{vw5JI}$ or Tn5-Mob, for example; and (d) by hybridizing the bacteria containing the plasmid with its incorporated marker gene with the recipient bacterium simultaneously with an auxiliary bacterium to promote transfer.

5 2. NON-LEGUME SEED COATINGS AND COATED SEEDS

In order to establish symbiosis between the Rhizobia transformants of the present invention, the seeds of the non-legume should be treated or coated with a material specific for the Rhizobium transformants. Such coatings may include or exclude the Rhizobium transformant itself. The presence or absence of the Rhizobia transformant in the coating impacts only on the method used to later establish symbiosis in the growing plant.

5.2.1. THE NON-LEGUME SEED COATING

The seed coating includes but is not limited to the following which may incorporate or exclude the Rhizobium transformant: (a) a mixture of extracts derived from each of the legume host plants which is a partner to each parent of the Rhizobia transformant; (b) chromatographic fractions derived from each legume host plant which is a partner to each parent Rhizobium of the transformant; (c) crystals derived from the legume extract and/or its chromatographic fractions or (d) proteins related thereto. As previously explained, the proteins can be produced via chemical synthetic methods, recombinant DNA techniques or isolated from alternate sources.

Although we are not bound to any theory or explanation of the invention, these seed coatings described above may contain any of a number of factors including but not limited to lectins, flovones, etc. which may be important in establishing the symbiosis between the non-legume and the Rhizobia transformant. Recently, expression of Rhizobium nodulin genes involved in normal root-hair curling, and, therefore, in symbiont-/host recognition and nodulation, was reported to be induced by a legume root exudate (Rossen et al., 1985, EMBO 4(13A):3369-3373). Very recently, a group of compounds called flavones which are secreted from legume roots were reported to induce expression of nodulation genes in Rhizobium (see Redmond et al., 1986, Nature 323: 632-635). Flavones are normally produced in flowers and leaves of various plants, only legumes are known to secrete or contain flavones in roots. According to the Redmond et al. report, certain flavones in the root exudate from pea, bean, soybean, alfalfa and clover induced expression of the nodA gene in *R. trifoli* while root exudate from the non-legumes maize, rice and Parasponia did not. The stimulation of the Rhizobium was not legume-host specific from a symbiotic point of view; i.e., the expression of nodA was induced in the Rhizobium in response to a number of different legume exudates. Therefore, the flavones may be one of the early signals between a Rhizobium and a legume after which a second more host specific recognition takes place (for example, the lectin-polysaccharide recognition system) to establish that particular host-symbiont partnership. Possibly the flavone induction system is an early event which enables the non-legume seeds treated with legume extracts to become receptive to infection with the $F_2$ Rhizobium transformants of the invention. Perhaps flavones present in the legume extracts are taken up by the non-legume seed during the imbibition or pregermination, transported to the root of the young seedling and when exuded attract the Rhizobium transformant.

Other factors from the legume extracts contained in the seed coatings herein may be important in the establishment of the non-legume host $F_2$ transconjugant infection. For example, the seed coatings may contain lectins which are believed to be involved in the specific recognition interaction between Rhizobia and their legume host partners. A recent report describes a particulate form of the lectin, Trifolin A, which can be isolated from clover root exudates and which specifically binds to *R. trifoli* (Truchet et al , 1986, Physiol. Plant 66: 575–582). Interestingly, legume root exudates containing lectin restored the ability of mutant Rhizobia to recognize and nodulate their legume host (see Halverson et al., 1984, Plant Physiol. 74: 84–89 and 1985, Plant Physiol. 77: 621 –625). Quite possibly one or more lectins are present in the seed coatings of the invention which enable the specific recognition between the Rhizobia transformant and its non-partner to take place.

5 2 2. METHODS FOR COATING THE NON-LEGUME SEEDS

The non-legume seeds may be coated by a variety of methods including but not limited to immersion and air drying, spraying, encapsulation (for example in polymers), immersion and drum drying, etc. The method chosen would depend upon the coating to be used. For example, if the Rhizobia transformant is included in the coating mixture, methods or ingredients which ensure the viability of the bacteria should be used; these include but are not limited to: coating mixtures which contain a gel material to keep the moisture levels high; alternatively, the seeds can be coated with pulverized seed husks which contain fungicides. In any case, the method should be accomplished so that the active materials in the coating are not denatured or destroyed.

In the examples of the present invention, the non-legume seeds were coated by immersion in the legume extracts and air drying; preferably three times. Two immersions resulted in poor penetration of the Rhizobia transformants, whereas four immersions did not seem to improve penetration.

5.3. ESTABLISHING SYMBIOTIC NITROGEN FIXATION IN THE NON-LEGUMES

A number of methods can be used to ensure infection of the non-legume by the Rhizobia transformants; the method chosen depends, in part, upon the nature of the non-legume seed coating used.

For example, non-legume seeds treated as described with a coating that does not contain the Rhizobium transformants can be watered with a suspension of the Rhizobium transformant. Thus the seed, seedling or plant can be watered with an appropriate volume of the bacterial suspension. Where the seed coating contains the Rhizobium transformant, only planting and watering are required.

It may be desirable to add non-nitrogenous fertilizers depending upon the type of plant, condition of the soil or terrain, etc. In fact, in the laboratory experiments we have found that the addition of 2 mM nitrogen at the initial sowing of the seeds is enough to increase the initial growth of the plant without harming or "shutting off" the Rhizobia transconjugants. This more closely simulates the natural condition since most soil (even unfertilized) contains some amount of nitrogen (no more that 2 mM); the addition of nitrogen in the field is not required.

5 4. THE NODULATED NON-LEGUMES

The non-legumes that are nodulated by the Rhizobia transformants of the present invention have a nitrogen content and dry matter content that is equal to or greater than their non-nodulated counterparts fertilized with nitrogen; the nodulated plants have a higher nitrogen content and dry matter content than their unfertilized non-nodulated counterparts. Analyses of the amino acid compositions of the nodulated plants revealed that in most cases the proportion of each amino acid remains the same but the total concentration per plant is increased. However, in some cases, higher levels of tryptophan and leucine have been observed.

Interestingly, we have found that the straw remaining after harvest of some of the nodulated non-legume species consistently had a protein content of about 6% to about 9%; this is in striking contrast to the protein content of 1.5% to 2% normally found in the straw of the non-nodulated counterparts. This high protein straw can advantageously be used as a protein source, for example, in animal feed mixtures for both farm and domestic animals.

The Rhizobium transformants of the present invention which nodulate and fix nitrogen in non-legumes can reduce the use of costly nitrogenous fertilizer and ultimately can improve the soil.

5.4.1. NODULE CHARACTERISTICS

The morphology of the non-legume nodules formed by the Rhizobia transformants of the present invention is quite normal in appearance, however, a larger proportion of smaller nodules are formed. The Rhizobia appear to enter the root via infection threads and the bacteroids seem to be maintained in compartments. In fact, a reddish color is observed in the nodule which may be leghemoglobin or a protein closely related thereto. Electron microscopy of the nodules revelas that the vascular bundles found in the cortex are peripherally located, whereas the vascular bundles of lateral roots are centrally located. Most of the cells in the central portion of the nodules are filled with bacteroids.

6. EXAMPLE:MATERIALS AND METHODS FOR THE PRODUCTION OF RHIZOBIA TRANSCONJUGANTS AND NODULATION OF NON-LEGUMES

The examples that follow describe the nodulation by Rhizobium transformants of the present invention of the following non-legumes belonging to the grass family (Poaceae): wheat, barley, sorghum and rice. In addition, a member of the Brassicas, a plant genus outside the grass family (i.e., the Cruciferae family) is also nodulated by a Rhizobium transformant of the present invention. Interestingly, a positive effect was observed on another plant outside the grass family, Eucalyptus (a member of the Myrtaceae family). In each example, the alternating line culture method was used to produce Rhizobium transconjugants. The non-legume seeds were coated by immersion of the seeds in legume extracts specific for the particular Rhizobium transconjugant used to nodulate the non-legume. The coated non-legume seeds were infected with the Rhizobia transconjugants by sowing the coated seeds, allowing them to germinate and watering the seedlings with a suspension of the Rhizobium transconjugant; nitrogen-fixing nodules developed in 8–12 weeks.

In the examples, laboratory studies were conducted in which the non-legumes were divided into three groups treated as follows: (a) the first group was treated with the Rhizobium transconjugant without nitrogenous fertilizer ($+R-N$); (b) the second group was treated with nitrogenous fertilizer without the Rhizobium transconjugant ($-R+N$); and (c) the third group was treated with neither the Rhizobium transconjugant nor nitrogenous fertilizer ($-R-N$). At certain times during growth, the plants were sampled and the total content of organic nitrogen per plant, the amount of dry matter per plant, and in some experiments the protein content per plant and its amino acid composition were determined. In some examples, field studies were conducted. The results demonstrated that, in each case, the non-legume plants nodulated by the Rhizobia transconjugants were able to fix nitrogen and did not require nitrogenous fertilizer for growth. In fact, in many cases, the nodulated non-legumes ($+R-N$) had a higher nitrogen content and dry matter content than either the fertilized non-nodulated group ($-R+N$) or the untreated group ($-R-N$).

Unless otherwise indicated, the materials and methods described below were used in each example that follows.

6.1. THE ALTERNATING LINE CULTURE METHOD

The alternating line culture method used in each example that follows involves the following: two different Rhizobia species (the parent generation) were streaked in alternating rows (3 mm apart) on a nutrient agar medium containing, in addition to nutrients necessary for growth, a non-denatured extract of each legume host specific for each parent Rhizobium. After incubation at a growth temperature below 32° C., e.g., between 18° C. and 30° C., each parent Rhizobium formed colonies having a color characteristic for that species; Rhizobia transconjugants ($F_1$ transconjugants) were produced between the alternating rows of the colored parent colonies. The Rhizobia $F_1$ transconjugants unlike their parents, formed milky white colonies and could not nodulate plants. It should be noted that incubation at a temperature above 32° C. on the agar medium used herein results in the formation of red colonies by all Rhizobia species streaked on the plate; however, if the temperature is lowered to a temperature below 32° C. (e.g., preferably between 18° C. to 30° C.) the characteristic color of each colony will reappear.

The Rhizobia $F_1$ transconjugants were isolated from the milky white colonies and cultured as described in alternating rows (3 mm apart) with a third Rhizobium parent species on nutrient agar medium containing, in addition to the non-denatured legume extracts used to produce the milky white colonies, a third non-denatured legume extract derived from the legume host specific for the third parent Rhizobium species. Rhizobia $F_2$ transconjugants were produced in between the alternating rows of the milky white colonies formed by the Rhizobium $F_1$ transconjugant and the colored colonies formed by the third parent Rhizobium. The Rhizobium $F_2$ transconjugant colonies were identified by their snowy white color; these $F_2$ transconjugants were able to infect, nodulate and fix nitrogen in non-legumes which were treated and planted as described. The materials and methods used to produce the Rhizobium transconjugants are described in more detail below.

6 1.1. ISOLATION OF PARENT RHIZOBIA

The Rhizobia species used as the parent generations were isolated either from soil samples or from legume nodules which were at an advanced stage of development.

Isolation of parent Rhizobia from the soil was accomplished by placing seeds of host legume plant which are nodulated by the Rhizobia in the soil samples. The plants were harvested after 3-4 weeks (normally) or 10-12 weeks if slow-growing.

Isolation of parent Rhizobia from legume nodules was accomplished as follows: the nodules were severed from the roots of the legume plant along with approximately 1 cm of the root tissue surrounding the nodule which was sterilized by immersion in 3% $HgCl_2$ and rinsed in 80% ethanol. The nodules were then excised from the root tissue and crushed in a mortar under aseptic conditions. The macerated material was spread on the nutrient agar medium described below. The colonies were purified by subculturing on a medium of the same composition until single colonies were formed twice. The Rhizobia isolated from the purified single colonies were streaked in alternating rows on the nutrient agar medium described in order to culture the alternating rows of parent Rhizobia colonies.

6.1.2. NUTRIENT AGAR MEDIUM

The agar medium used to culture the Rhizobia in alternating lines was prepared by adding the following nutrients in the amounts indicted to 100 ml distilled water:

| | |
|---|---|
| $KH_2PO_4$ | 0.15 g |
| $K_2HPO_4$ | 0.15 g |
| $KNO_3$ | 2.50 g |
| $(NH_4)_2SO_4$ | 0.135 g |
| $MgSO_4.7H_2O$ | 0.25 g |
| Mannitol | 10.00 g |
| Agar | 12.00 g |
| Solution No. 1 | 1.00 ml |
| Yeast extract | 5.00 ml |

Solution No. 1 had the following composition:

| | |
|---|---|
| $MnCl_2.4H_2O$ | 500 mg |
| $H_3BO_3$ | 300 mg |
| $ZnSO_4.2H_2O$ | 200 mg |
| $NaMoO_4.2H_2O$ | 20 mg |
| $CuSO_4.5H_2O$ | 2 mg |
| $CoCl_2.6H_2O$ | 2 mg |
| Distilled water to a final volume of 100 ml | |

The agar medium defined above was then autoclaved for 20 minutes at 2 bar and cooled to a temperature between 55° C. and 60° C. upon which the following was added:1.0 ml of each Solution No. 2, Solution No. 3 and Solution No. 4; 20 ml each of non-denatured legume plant extracts derived from the host legume plant specific for each parent Rhizobia to be cultured on the media; and 15 mg of each of the following amino acids: L-alanine, L-serine and L-tryptophan. To avoid denaturing the proteins in the legume extract the final media composition should not be autoclaved.

Solution No. 2, Solution No. 3 and Solution No. 4, had the compositions indicated below. Each was prepared using sterile distilled water.

| | |
|---|---|
| Solution No. 2: | |
| Nicotinic acid | 50 mg |
| Thiamine HCl | 50 mg |
| Pyridoxin HCl | 50 mg |
| Myoinositol | 50 mg |
| Biotin | 50 mg |
| Sterile distilled water to final volume of 100 ml | |
| Solution No. 3: | |
| Potassium Iodate | 75 mg |
| Sterile distilled water | 100 ml |
| Solution No. 4: | |
| $CaCl_2.H_2O$ | 15 gm |
| Sterile distilled water | 100 ml |

6.1.3. LEGUME PLANT EXTRACT

The legume plant extracts used in the agar medium and for coating the non-legume seeds were prepared as described below.

The whole plant, or selected plant parts, e.g. clean washed roots, sterilized seeds or aerial parts, or preferably, young shoots, were divided into fine particles, ground in a mortar with 80% ethanol to a think, homogeneous paste into which was added an equal volume of potassium-sodium salt buffer, pH 7.2, comprising the following:

| | |
|---|---|
| $K_2HPO_4$ | 0.430 g |
| $NaH_2PO_4$ | 1.469 g |
| NaCl | 7.200 g |
| Sterile distilled water to a final volume of 1000 ml | |

The mixture of the homogenized plant extract and buffer was allowed to rest for 48 hours at 4° C. and was pelleted by centrifugation at approximately 5000× g for 30 minutes. Then, the supernatant was dialyzed against sterile distilled water at 4° C. for about 48 hours, during which time the water was replaced 5 to 6 times, until a clear, colorless liquid, i.e., the extract, was obtained. The extracts were stored at 4° C.

6.1.4. ISOLATION OF RHIZOBIA TRANSCONJUGANTS

When the two parent Rhizobia were cultured at a temperature below 32° C. in alternating lines (3 mm apart) on the agar medium containing the appropriate legume extracts as described above, the parent Rhizobia formed colonies having a characteristic color. However, between the rows of colored parent colonies two types of colonies developed: (a) colonies having a color which is a mixture of the colors of the parent colonies and (b) the milky white colonies of the Rhizobium $F_1$ transconjugant. The proportion between the colored colonies and the $F_1$ transconjugant milky white colonies varied somewhat but on the average ranged from about 100:3 (mixed colored colonies: milky white colonies). The mixed colored colonies nodulated both host legume species, but only in one generation; i.e., the Rhizobia of the mixed colored colonies nodulated the legume host partners of both parent Rhizobia but the Rhizobia recovered from the nodules of each legume host could only nodulate that particular legume host again. By contrast, the $F_1$ transconjugant milky white colonies do not nodulate any plant.

Since it was difficult to transfer a single hybrid colony to a new medium without polluting it with one or more colored colonies, a biological cleaning was performed one or more times by transferring the milky white colonies to another agar medium (of the same composition) until, typically after 10 to 12 weeks, a pure culture of the $F_1$ transconjugant with a stable and uniform milky white colour was obtained.

The pure culture of $F_1$ transconjugant which formed the milky white colonies was then cultured at a temperature below 32° C. in alternating lines (3 mm apart) with another Rhizobium species on an agar medium of the same composition used for the $F_1$ transconjugant, which contained in addition, a third legume extract derived from the legume host specific for the third parent Rhizobium. The $F_1$ transconjugant produced its characteristic milky white colonies whereas the parent Rhizobium produced colonies having its specific color. Two types of colonies developed between the lines of milky white colonies and the colored colonies: colored colonies and snowy white colonies. The snowy white colonies comprise the Rhizobium $F_2$ transconjugants which can form nitrogen fixing nodules in non-legumes. The $F_2$ transconjugant snowy white colonies were cleaned and isolated as described for the milky white colonies and were used to nodulate non-legumes.

After nodulation of the non-legume plant, the Rhizobia $F_2$ transconjugant bacteroids can be isolated from the nodule and cultured in an agar medium. If the agar medium has the same composition as the agar medium used to produce the transconjugant (i.e., the agar medium contains the three legume extracts derived from the legume host specific for each parent Rhizobium used to produce the $F_2$ transconjugant) plus an extract of its non-legume host plant, then the $F_2$ transconjugants isolated from the non-legume nodule will form colonies having a greyish color.

6.2. PREPARATION OF THE NON-LEGUME SEEDS

Seeds of the non-legume plant were coated by immersion three times at 20° C. for 3 hours each time in an aqueous solution containing 3% calcium sulphate, and up to 10% a mixture of the three legume extracts, prepared as described in Section 6.1.3., which were used to produce the Rhizobium $F_2$ transconjugant. After each immersion the seeds were air dried at 40° C. for 12 hours.

6.3. INFECTION OF NON-LEGUMES WITH RHIZOBIA $F_2$ TRANSCONJUGANTS

Infection of non-legumes with Rhizobia $F_2$ transconjugants was accomplished by sowing the coated non-legume seeds and watering the germinated seedlings with a suspension of the Rhizobium $F_2$ transconjugant. In the examples that follow, laboratory studies and field studies were conducted in which the germinated seedlings were treated with either (a) the Rhizobium $F_2$ transconjugant without inorganic nitrogen fertilizer $(+R-N)$; (b) inorganic nitrogen fertilizer without the Rhizobium $F_2$ transconjugant $(-R+N)$; or (c) neither the Rhizobium $F_2$ transconjugant nor the inorganic nitrogen fertilizer $(-R-N)$. The nitrogen content per plant, the dry weight and in some cases the amino acid composition of the resulting plants were determined.

The materials and methods used are described in greater detail below.

6.3.1. LABORATORY STUDIES

In the laboratory studies, the coated non-legume seeds were sown in one liter containers (Jydsk Papir Vaerk, Arhus) filled with 3mm "Fibo"(R)-clinkers; 4 to 5 seeds per container were sown. The "Fibo" clinkers are air filled, burnt clay pebbles of approximately 3 mm in diameter which are normally used as isolation material.

When the germinated seeds grew a few centimeters above the "Fibo" clinker surface the seedlings in each container were watered as follows: (a) the $+R-N$ group were watered with a 50 ml suspension of the Rhizobium $F_2$ transconjugant; thereafter the plants were watered once a week with 50-80 ml per container of a non-nitrogenous fertilizer; (b) the $-R+N$ group were not treated with the Rhizobium $F_2$ transconjugant but instead were watered with an inorganic nitrogen fertilizer; thereafter the plants were watered once a week with 50-80 ml per container of the same inorganic nitrogen fertilizer; and (c) the $-R-N$ group were watered with 50-80 ml per container of the non-nitrogenous fertilizer. The inorganic nitrogen fertilizer and non-nitrogenous fertilizer used are defined below.

| STOCK SOLUTIONS | | Fertilizer ml Stock Soln/liter Final Volume | |
|---|---|---|---|
| | | Nitrogenous | Non-Nitrogenous |
| $NH_4NO_3$ | (1.0 M) | 20 | 0 |
| $CaSO_4.2H_2O$ | (0.012 M) | 65 | 65 |
| $KH_2PO_4$ | (0.10 M) | 20 | 20 |
| $MgSO_4.7H_2O$ | (0.20 M) | 15 | 15 |
| Fe(EDTA): | | | |
| $FeSO_4.7H_2O$ | (2.490 g) | 10 | 10 |
| $Na_2$ EDTA | (3.716 g) | | |
| Final Volume 1 liter | | | |
| $MnCl_3.4H_2O$ | (106.1 mg/l) | 10 | 10 |
| $H_3BO_3$ | (142.2 mg/l) | 10 | 10 |
| $ZnSO_4.7H_2O$ | (110.7 mg/l) | 10 | 10 |
| $CuSO_4.5H_2O$ | (8.0 mg/l) | 10 | 10 |
| $Na_2MoO_4.2H_2O$ | (11.1 mg/l) | 10 | 10 |

The suspensions of Rhizobia $F_2$ transconjugants which were used to water the seedlings were produced by culturing the Rhizobium $F_2$ transconjugant in 300 ml flasks containing 200 ml of the following nutrient medium:

| | |
|---|---|
| $KH_2PO_4$ | 1.0 g |

-continued

| | |
|---|---|
| $K_2HPO_4$ | 1.0 g |
| $MgSO_4.7H_2O$ | 0.36 g |
| $CaSO_4.2H_2O$ | 0.17 g |
| $FeCl_3.6H_2$ | 0.005 g |
| $KNO_3$ | 0.7 g |
| Yeast extract | 1.0 g |
| Mannitol | 3.0 g |
| Distilled water to a final volume of 1000 ml | |

The bacteria were grown at 28° C. for two to three days until the bacterial density of the culture measured spectrophotometrically at $OD_{620}$ was 0.8, thus indicating that the bacteria were in the logarithmic growth phase and the culture had not entered the stationary phase. Then the cells were pelleted by centrifugation at approximately $5,000 \times$ g for 30 minutes and washed by resuspension in sterile water. This wash was repeated once or twice in order to remove all nitrogenous compounds from the bacterial cells. The final pellet of cells was resuspended in 1.8 liter sterile water; this final bacterial suspension was used to water the non-legume seedlings.

6.3.2. FIELD STUDIES

In the field studies, the coated non-legume seeds were sown in soil that had never been cultivated. The land was cleared and divided into strips that were 30 feet wide by 90 feet long. The seeds were sown only in alternate strips (i.e., strips of unsown land remained in between the strips where the seeds were sown) in order to prevent chemicals leaching out of one strip from entering and contaminating another strip. Within a strip, the seeds were sown in six rows; each row was separated by 60 inches and the seeds within each row were sown 8 inches apart.

Each strip contained one of the following groups: (a) the $+R-N$ group which was treated with the Rhizobium $F_2$ transconjugant and watered with the previously defined non-nitrogenous fertilizer, (b) the $-R+N$ group which was not treated with the Rhizobium $F_2$ transconjugant but instead was watered with the previously defined inorganic nitrogen fertilizer; and (c) the $-R-N$ group which was neither treated with the Rhizobium $F_2$ transconjugant nor the inorganic nitrogen fertilizer but instead was watered with the non-nitrogenous fertilizer.

The following procedure was used to infect the $+R-N$ group with the Rhizobium $F_2$ transconjugant: a culture of the Rhizobium $F_2$ transconjugant was inoculated 4 inches below each seed that was sown. The sowing and inoculation of the soil was accomplished by a machine which had a 300 gallon tank containing a suspension of the Rhizobia $F_2$ transconjugant prepared as previously described on a much larger scale (i.e., the Rhizobia $F_2$ transconjugant was grown to log phase in a 10,000 gallon tank and diluted to an $O.D._{620}$ of 0.8). Approximately 1.5 ml/seed of the Rhizobium $F_2$ transconjugant culture was inoculated into the underlying soil. Thereafter the seeds and seedlings were watered as described.

6.4. PROTOCOL FOR ANALYSIS OF DRY MASS, NITROGEN CONTENT AND PROTEIN CONTENT OF NODULATED NON-LEGUMES

Periodically a number of containers from each plant group in the laboratory studies were thinned out to 3 plants per container and removed for Kjeldahl-analysis in which the total content of organic nitrogen and the amount of dry matter per container (i.e., per 3 plants) was determined. To this end, the aerial parts of the plants were removed, dried for 48 hours at 80° C., weighed, crushed and ground in a mortar. Samples of the macerated material were removed for the Kjeldahl-analysis, which was carried out according to the standard method. Each Kjeldahl-analysis was repeated from 4 to 6 times. The results were recorded in terms of weight of nitrogen and weight of dry matter per plant. In all cases the Rhizobium nodulated plants had a higher content of dry matter and nitrogen than did the nitrogen fertilized or untreated groups.

In the field studies, a number of plants were harvested periodically and the protein content per plant was determined by first assaying the nitrogen content per plant using the Kjeldahl analysis and multiplying the percent nitrogen by a factor of 6.25. In some studies, the amino acid composition of the protein was determined. In all cases the Rhizobium nodulated non-legumes had a higher protein content than that of the plants which were treated with the inorganic nitrogen fertilizer and the plants which were treated with the non-nitrogenous fertilizer.

7. EXAMPLE: RHIZOBIUM TRITICI WHICH NODULATES WHEAT

*Rhizobium tritici*, which nodulates wheat, was produced according to the method described in Section 6 by first crossing *R. phaseoli* with *R. cowpea leucaena* to produce the $F_1$ transconjugant which was then crossed with *R. trifoli*. The *R. tritici* thus produced was used to nodulate four types of wheat: Anja, Kraka, Vuka and Williams.

7.1. PREPARATION OF RHIZOBIUM TRITICI

For the production of *R. tritici* the following parent Rhizobia were used to produce the $F_1$ transconjugant milky white colonies: (a) *R. phaseoli*, isolated from a kidney bean cultivar, Prospector, grown in a soil sample found near Aarhus, MS-1; and (b) *R. cowpea leucaena*, isolated from the tropical tree *Leucaena leucocephala* (belonging to the family of Fabaceae) from Papua, New Guinea.

The parent Rhizobia were cultured in alternating lines on the agar medium previously described; the legume extracts used in the medium were derived from the aerial parts of the kidney bean and from the leaves of the *Leucaena leucocephala*, respectively. The colonies formed by *R. phaseoli* had a characteristic dark brown color whereas the colonies formed by *R. cowpea leucaena* had a characteristic greyish brown color.

The Rhizobium $F_1$ transconjugant derived from the milky white colonies was cleaned and cultured as described in alternating lines with a strain of *R. trifoli* which was isolated from red clover, grown in a soil sample found in the vicinity of Randers. The legume extracts used in the medium were derived from the aerial parts of the kidney bean, the leaves of *Leucaena leucocephala* and the aerial parts of red clover. The colonies formed by the F $_1$ transconjugant were milky white whereas the colonies formed by *R. trifoli* had a characteristic light brown color.

The Rhizobium $F_2$ transconjugant derived from the snowy white colonies obtained in between the streaks, herein called *Rhizobium tritici*, was cleaned and isolated as described; this took approximately 20 weeks, and then the F₂ transconjugant was used to nodulate wheat.

7.2. NODULATION OF WHEAT WITH RHIZOBIUM TRITICI

The *Rhizobium tritici* was used to nodulate four types of wheat: Anja, Kraka, Vuka and Williams. The wheat seeds were treated by immersion three times in the aqueous solution previously described containing 3% calcium sulphate and up to approximately 10% legume extracts which were used to produce the *R. tritici;* i.e., the three legume extracts used to coat the seeds were derived from the aerial parts of the kidney bean, the leaves of *Leucaena leucocephala* and the aerial parts of red clover. After each immersion the seeds were air-dried and sown as described below.

7.2.1. LABORATORY STUDY

The experimental protocol previously described was carried out for three types of wheat used: Anja, Kraka and Vuka; i.e., 4 to 5 coated seeds were sown per one liter container filled with "Fibo"-clinkers and allowed to germinate. Each of the three types of wheat was divided into the following three groups; (a) +R−N, the seedlings of which were watered with a 50 ml suspension of *R. tritici* prepared as previously described, followed by weekly watering with the non-nitrogenous fertilizer; (b) −R+N, the seedlings of which received no *R. tritici* but were watered with the inorganic nitrogen fertilizer; and (c) −R−N, the seedlings of which received neither the *R. tritici* nor inorganic nitrogen fertilizer and instead were watered with the non-nitrogenous fertilizer previously described. The plants treated with *R. tritici* developed root nodules in 8 to 10 weeks. The plants in each container were thinned to three plants, and ten containers were used in each group for analysis of dry mass and nitrogen content.

7.2.2. FIELD STUDY

For the field study, the coated wheat seeds were sown as described in Section 6.3.2. The seeds of lot (a) +R−N, were treated as described with a suspension of *R. tritici* and were watered with non-nitrogenous fertilizer; those of lot (b) −R+N, were not treated with *R. tritici* but were watered with the inorganic nitrogen fertilizer; and those of lot (c) −R−N, were not treated with either *R. tritici* or the inorganic nitrogen fertilizer, and were simply watered with the non-nitrogenous fertilizer.

7.3. ANALYSIS OF DRY MASS, NITROGEN CONTENT AND PROTEIN CONTENT OF THE NODULATED WHEAT

The analytical methods described in Section 6.4 were used to characterize the nodulated wheat plants.

7.3.1. RESULTS OF LABORATORY STUDY

The wheat plants were harvested from the containers at 56, 70, 87, 100 and 118 days after sowing. The dry weight per plant and nitrogen content per plant (Kjeldahl analysis) were analyzed as previously described.

The results are shown in FIG. 1 in which the dry weight per plant (A) and nitrogen content per plant (B) are plotted over the number of days after sowing.

In order to facilitate the understanding of the figure, the following information about the average weight of dry matter and average content of nitrogen for the three wheat types is helpful:

| Wheat | Dry matter grams per 100 seeds | Nitrogen mg per seed |
|---|---|---|
| Anja | 4.403 | 1.103 |
| Kraka | 3.611 | 0.896 |
| Vuka | 4.052 | 0.819 |

The number of harvested plants at the various time points were:

| Plant Group | Number of Plants Harvested Days After Sowing | | | | |
|---|---|---|---|---|---|
| | 56 | 70 | 87 | 100 | 118 |
| Trial One: | | | | | |
| +R−N | 33 | 30 | 21 | 23 | 25 |
| −R+N | 24 | 30 | 20 | 21 | 20 |
| −R−N | 24 | 26 | 22 | 26 | 35 |
| Trial Two: | | | | | |
| +R−N | 11 | 10 | 7 | 8 | 8 |
| −R+N | 8 | 10 | 7 | 7 | 7 |
| −R−N | 8 | 9 | 7 | 9 | 12 |

The results shown in FIG. 1 demonstrate that during the growth period the Rhizobium treated wheat plants had a higher content of nitrogen and dry matter than the plants which were fertilized with nitrogen; at the termination of the experiment the dry content of the +R−N plants was almost 40% higher than that of the −R+N plants and both of these categories had a higher weight than the untreated −R−N wheat plants.

7.3.2. RESULTS OF FIELD STUDY

The wheat plants in the field study were harvested after one season of growth and the protein content per plant was analyzed as previously described. The results shown in Table II clearly demonstrate that the plants treated with *R. tritici* (+R−N) had a higher protein content than either the group treated with inorganic nitrogen fertilizer (−R+N) or the group treated with non-nitrogenous fertilizer (−R−N).

TABLE II

| PROTEIN CONTENT OF WHEAT | |
|---|---|
| Plant Group | Protein Content per Plant |
| +R−N | 22-28% |
| −R+N | 12-14% |
| −R−N | ND* |

* ND; No data; these untreated plants died after 8 weeks.

8. EXAMPLE: RHIZOBIUM HORDEI WHICH NODULATES BARLEY

*Rhizobium hordei* which nodulates barley, was produced according to the method described in Section 6 by first crossing *R. phaseoli* with *R. leguminosarum* to produce the F₁ transconjugant which was then crossed with *R. cowpea* leucaena. The *R. hordei* thus produced was used to nodulate four types of barley: Hasso, Cerise, Harry and Igri.

8.1 PREPARATION OF RHIZOBIUM HORDEI

For the production of *R. hordei* the following parent Rhizobia were used to produce the F₁ transconjugant milky white colonies: (a) *R. phaseoli,* isolated from a kidney been cultivar, Prospector, grown in a soil sample found near Aarhus; and (b) *R. lequminosarum,* isolated from garden pea.

The parent Rhizobia were cultured in alternating lines on the agar medium previously described; the legume extracts used in the medium were derived from the aerial parts of the kidney bean and of the garden pea, respectively. The colonies formed by *R. phaseoli* had a characteristic dark brown color whereas the colonies formed by *R. leguminosarum* had a characteristic golden yellow.

The Rhizobium $F_1$ transconjugant derived from the milky white colonies was cleaned and cultured as described in alternating lines with a strain of *R. cowpea leucaena* which was isolated from the tropical tree *Leucaena leucocephala*. The legume extracts used in the medium were derived from the aerial parts of the kidney bean, the garden pea and the leaves of *Leucaena leucocephala*. The colonies formed by the $F_1$ transconjugant were milky white whereas the colonies formed by *R. cowpea leucaena* had a characteristic greyish brown color.

The Rhizobium $F_2$ transconjugant derived from the snowy white colonies obtained in between the streaks, herein called *Rhizobium hordei*, was cleaned and isolated as described. The $F_2$ transconjugant was used to nodulate barley.

8.1.1. CHARACTERIZATION OF RHIZOBIUM HORDEI

Plasmid DNA of the three parent strains, the $F_1$ transconjugant, and the $F_2$ transconjugant (*R. hordei*) were isolated using a modification of the method of Hirsch et al. (1980, J. Gen. Microbiol. 120: 403-412) which involved lysing the Rhizobia by an overnight incubation at 4° C. in 40% SDS (sodium dodecyl sulfate), isolating the plasmid DNA which was separated by electrophoresis in 0.7% agarose gels. Results of such analysis revealed that the *R. hordei* had additional plasmids of low molecular weight that were not observed in the three parent Rhizobia or the $F_1$ transconjugant.

8.2. NODULATION OF BARLEY WITH RHIZOBIUM HORDEI

The *Rhizobium hordei* was used to nodulate four types of barley: Hasso, Cerise, Igri and Harry. The barley seeds were treated by immersion three times in the aqueous solution previously described containing 3% calcium sulphate and up to approximately 10% legume extracts which were used to produce the *R. hordei*; i.e., the legume extracts used to coat the seeds were derived from the aerial parts of the kidney bean, garden pea and the leaves of *Leucaena leucocephala*. After each immersion the seeds were air-dried and sown as described below.

8.2.1. LABORATORY STUDY

The experimental protocol previously described was carried out for each type of barley used; i.e., 4 to 5 coated seeds were sown per one liter container filled with "Fibo"-clinkers and allowed to germinate. Each type of barley was divided into the following three groups; (a) +R−N, the seedlings of which were watered with a 50 ml suspension of *R. hordei* prepared as previously described, followed by weekly watering with the non-nitrogenous fertilizer; (b) −R+N, the seedlings of which received no *R. hordei* but were watered with the inorganic nitrogen fertilizer; and (c) −R−N, the seedlings of which received neither the *R. hordei* nor the inorganic nitrogen fertilizer but instead were watered with the non-nitrogenous fertilizer. The plants treated with *R. hordei* developed root nodules in 8 to 10 weeks. The plants in each container were thinned to three plants each and ten containers were used in each group for analysis of dry mass and nitrogen content.

8.3. ANALYSIS OF DRY MASS, NITROGEN CONTENT AND PROTEIN CONTENT OF THE NODULATED BARLEY

The analytical methods described in Section 6.4. were used to characterize the nodulated barley plants.

8.3.1. RESULTS OF LABORATORY STUDY

The plants were harvested from the containers at 59, 71, 85, 108 and 128 days after sowing. The dry weight per plant and nitrogen content per plant (Kjeldahl analysis) were analyzed as previously described.

The results are shown in FIG. 2 in which the dry weight per plant (A) and nitrogen content per plant (B) are plotted over the number of days after sowing.

In order to facilitate the understanding of the figure, the following information about the average dry matter weight and average contents of nitrogen of each barley type is helpful:

| Barley | Dry matter grams per 100 seeds | Nitrogen mg per seed |
|---|---|---|
| Hasso | 3.922 | 0.732 |
| Cerise | 4.217 | 0.792 |
| Igri | 3.932 | 0.775 |
| Harry | 5.068 | 0.826 |

The number of harvested plants at the various time points were:

| Plant Group | Number of Plants Harvested Days After Sowing | | | | |
|---|---|---|---|---|---|
| | 59 | 71 | 85 | 108 | 128 |
| Trial One: | | | | | |
| +R−N | 23 | 23 | 27 | 31 | 37 |
| −R+N | 17 | 14 | 30 | 23 | 40 |
| −R−N | 14 | 18 | 28 | 20 | 32 |
| Trial Two | | | | | |
| +R−N | 8 | 8 | 9 | 10 | 12 |
| −R+N | 6 | 5 | 10 | 8 | 13 |
| −R−N | 5 | 6 | 9 | 7 | 11 |

The results shown in FIG. 2 demonstrates that during the growth period the Rhizobium treated plants had a higher content of nitrogen and dry matter than the plants which were fertilized with nitrogen. At the temperature of the experiment the dry content of the +R−N plants was almost 18-22% higher than that of the −R+N plants and both of these categories had a higher weight than the −R−N barley plants treated with non-nitrogenous fertilizer.

8.4. $^{15}$ENRICHMENT IN NODULATED BARLEY

A barley plant was incubated in the presence of atmospheric $^{15}$N after which parts of the plant were assayed for $^{15}$N content as an indication of nitrogen fixation. More particularly, a barley plant (age 95 days) with small nodules was placed in a chamber so that the roots were incubated in the presence of atmospheric $^{15}$N for 23 hours. The atmosphere in the root chamber contained 80% $N_2$ (in which $^{15}$N was 12.85 At%) and 20% $O_2$. After the incubation period, samples were analyzed for $^{15}N$ content and the total nitrogen content of the plant was determined using the Kjeldahl method. Results are shown in Table III below.

TABLE III

| | NITROGEN CONTENT OF NODULATED BARLEY PARTS | | |
|---|---|---|---|
| Plant Part | Dry Wt (g) | N (mg/g) | Total N (mg) |
| Roots | 0.448 | 8.9 | 3.99 |
| Shoots | 1.017 | 7.5 | 7.63 |
| Whole Plant | 1.465 | 7.93 | 11.62 |

| | $^{15}N$ CONTENT OF NODULATED BARLEY PARTS | |
|---|---|---|
| | Number of Samples | At % $^{15}N$* |
| Roots | 4 | 0.450 ± 0.011 |
| Shoots | 3 | 0.392 ± 0.003 |

*$^{15}N$ content in atmospheric air is about 0.370 At %.

The data in Table III demonstrate that both the roots and shoots of the nodulated barley plant contain significantly more $^{15}N$ than does the atmosphere. These results indicate that nitrogen fixation took place in the nodulated barley plant.

8.5. MORPHOLOGY OF THE BARLEY NODULES

Electron microscopy was performed on some of the large nodules; this involved the examination of ultrathin cross-sections stained with uranyl acetate and lead citrate. The cellular organization of the barley nodules was the same as the organization reported by Newcomb (1976, Can J. Bot. 54: 2163-2186) for pea nodules; i.e., the vascular bundles were found in the peripheral cortex while the central part of the nodule was occupied by bacteroid-filled plant cells.

A further study involving light microscopy and electron microscopy (both scanning and transmission) of the surface of small barley nodules and the surface and transections of large barley nodules was conducted. The morphologies observed were compared to those of pea, white clover and soybean. Small barley nodules were visible when the plants reached about 50 days growth and formed on approximately 75% of the plants (this observation was made for wheat plants as well). Large barley nodules were observed at 89 to 110 days growth. The large barley nodules were rare but unmistakable; these measured approximately 2 to 4 mm in length and 1 to 2 mm in diameter and occurred on the main root at a location of about 2 to 6 cm below the position of the old seed. Eleven of thirteen large nodules which were dissected were red-brown in color inside, i.e., the same coloration as leghemoglobin in legume nodules at about 20-35 days old. Of the remaining two large nodules dissected, one was white and appeared as a young immature legume nodule and the other was green, just as a senescing legume nodule. Possibly, barley infection occurs in two stages: in the initial stage the R. hordei enters the root but does not elicit a nodule response; in the next stage formation of the nodule begins after a lag-period.

8.6. ANTIBIOTIC RESISTANCE OF REISOLATED BARLEY BACTEROIDS

Bacteria were reisolated from the large barley nodules and tested for antibiotic resistance. The reisolated bacteria were resistant to spectinomycin dihydrochloride at a concentration of up to 400 ug/ml. The R. hordei $F_2$ transconjugant originally used to infect the barley plants (i.e., the inoculant) exhibits the same resistance. Both the inoculant and the reisolate formed white opaque colonies when grown on ordinary yeast-mannitol agar.

One of the parents of the R. hordei $F_2$ transconjugant is also resistant to spectinomycin dihydrochloride to the same concentration. This parent is the R. leguminosarum strain MA1 which forms light yellow opaque colonies when grown on ordinary yeast-mannitol agar. The spectinomycin resistance gene is not resident on the Sym plasmid therefore, the R. hordei $F_2$ transconjugant appears to be a hybrid which contains a non-symbiotic plasmid or the main chromosome of the parent R. lequminosarum MA1. However, this does not exclude the possibility that the R. hordei $F_2$ transconjugant may also harbor the Sym plasmid of MA1.

9. EXAMPLE: RHIZOBIUM SORGHI WHICH NODULATES SORGHUM

Rhizobium sorghi which nodulates sorghum, was produced according to the method described in Section 6 by first crossing R. lupini with R. cowpea leucaena to produce the $F_1$ transconjugant which was then crossed with R. meliloti. The R. sorghi thus produced was used to nodulate three types of sorghum: Safra, Dabar and Feterita.

9.1. PREPARATION OF RHIZO

For the production of R. sorghi the following parent Rhizobia were used to produce the $F_1$ transconjugant milky white colonies: (a) R. lupini, isolated from lupine found in central Jutland; and (b) R. cowpea leucaena, isolated from the tropical tree Leucaena leucocephala (belonging to the family of Fabaceae) from Papua, New Guinea.

The parent Rhizobia were cultured in alternating lines on the agar medium previously described; the legume extracts used in the medium were derived from lupine and from the leaves of the Leucaena leucocephala, respectively. The colonies formed by R. lupini had a characteristic light yellow color whereas the colonies formed by R. cowpea leucaena had a characteristic greyish brown color.

The Rhizobium $F_1$ transconjugant derived from the milky white colonies was cleaned and cultured as described in alternating lines with a strain of R. meliloti which was isolated from alfalfa found in Stahr. The legume extracts used in the medium were derived from the lupine, the leaves of Leucaena leucocephala and the alfalfa. The colonies formed by the $F_1$ transconjugant were milky white whereas the colonies formed by R. meliloti had a characteristic yellowish brown color.

The Rhizobium $F_2$ transconjuqant derived from the snowy white colonies obtained in between the streaks, herein called Rhizobium sorghi was cleaned and isolated as described. The $F_2$ transconjugant was used to nodulate sorghum.

9.2. NODULATION OF SORGHUM WITH RHIZOBIUM SORGHI

The Rhizobium sorghi was used to nodulate three types of sorghum: Safra, Dabar and Feterita. The sorghum seeds were treated by immersion three times in the aqueous solution previously described containing 3% calcium sulphate and up to approximately 10% legume extracts which were used to produce the R. sorghi; i.e., the legume extracts used to coat the seeds were derived from the lupine, the leaves of *Leucaena leucocephala*, and the alfalfa. After each immersion the seeds were air-dried and sown as described below.

9.2.1. LABORATORY STUDY

The experimental protocol previously described was carried out for Safra, Dabar and Feterita sorghum i.e., 4 to 5 coated seeds were sown per one liter container filled with "Fibo"-clinkers and allowed to germinate. Each type of sorghum was divided into the following three groups: (a) +R−N, the seedlings of which were watered with a 50 ml suspension of *R. sorghi* prepared as previously described, followed by weekly watering with the non-nitrogenous fertilizer; (b) −R+N, the seedlings of which received no *R. sorghi* but were watered with the inorganic nitrogen fertilizer; and (c) −R−N, the seedlings of which received neither the *R. sorghi* nor the inorganic nitrogen fertilizer but instead were watered with the non-nitrogenous fertilizer. The plants treated with *R. sorghi* developed root nodules in 10 weeks. The plants in each container were thinned to three plants and ten containers were used in each group for analysis.

9.2 2. FIELD STUDY

For the field study, the coated sorghum seeds (the Feterita strain) were sown as described in Section 6.3.2. The seeds of lot (a) +R−N were treated as described with a suspension of *R. sorghi* and were watered with non-nitrogenous fertilizer; those of lot (b) −R+N, were not treated with *R. sorghi* but were watered with the inorganic nitrogen fertilizer; and those of lot (c) −R−N, were not treated with either *R. sorghi* or the inorganic nitrogen fertilizer, and were simply watered with the non-nitrogenous fertilizer.

9.3. ANALYSIS OF DRY MASS, NITROGEN CONTENT AND PROTEIN CONTENT OF THE NODULATED SORGHUM

The analytical methods described in Section 6.4. were used to characterize the nodulated sorghum plants.

9.3.1. RESULTS OF LABORATORY STUDY

The plants were harvested at from 76 to 152 days after sowing. The dry weight per plant and nitrogen content per plant (Kjeldahl analysis) were analyzed as previously described.

The following information about the sorghum average dry matter weight and average contents of nitrogen is helpful:

| Sorghum | Dry matter grams per 100 seeds | % Nitrogen per seed |
|---|---|---|
| Safra | 3.724 | 2.32 |
| Dabar | 2.944 | 2.17 |
| Feterita | 3.840 | 1.42 |

The number of harvested plants at the various time points were:

| Plant Group | Total Number of Plants Harvested at 76 to 152 Days After Sowing |
|---|---|
| +R−N | 121 |
| −R+N | 62 |
| −R−N | 70 |

9.3.2. RESULTS OF FIELD STUDY

The sorghum plants in the field study were harvested after one season of growth and the protein content per plant as well as the amino acid composition were analyzed as previously described. The results shown in Table IV clearly demonstrate that the plants treated with *R. sorghi* (+R−N) had a higher protein content than either the group treated with nitrogenous fertilizer (−R+N) or the untreated group (−R−N).

The analysis of the amino acid composition demonstrated that the relative amino acid composition of the Rhizobium treated plants is about the same as that of the nitrogen fertilized plants; however tryptophan and leucine seem to be elevated in the Rhizobium treated plants.

TABLE IV
PROTEIN CONTENT OF SORGHUM

| Plant Group | Protein Content of Seeds per Plant |
|---|---|
| +R−N | 34–52% |
| −R+N | 16% |
| −R−N | 4%* |

*Since the −R−N group died after 14 weeks, no seed could be obtained. The nitrogen and protein content of the plants were determined as described.

10. EXAMPLE: RHIZOBIUM ORYZAE WHICH NODULATES RICE

*Rhizobium oryzae*, which nodulates rice, was produced according to the method described in Section 6 by first crossing *R. meliloti* with *R. cowpea leucaena* to produce the $F_1$ transconjugant which was then crossed with *R. trifoli*. The *R. oryzae* thus produced was used to nodulate rice.

10.1. PREPARATION OF RHIZOBIUM ORYZAE

For the production of *R. oryzae* the following parent Rhizobia were used to produce the $F_1$ transconjugant milky white colonies: (a) *R. meliloti*, isolated from alfalfa found in the vacinity of Victoria; and (b) *R. cowpea leucaena*, isolated from the tropical tree *Leucaena leucocephala* (belonging to the family of Fabaceae) from Papua, New Guinea.

The parent Rhizobia were cultured in alternating lines on the agar medium previously described; the legume extracts used in the medium were derived from the alfalfa and from the leaves of the *Leucaena leucocephala*, respectively. The colonies formed by *R. meliloti* had a characteristic yellowish brown color whereas the colonies formed by *R. cowpea leucaena* had a characteristic greyish brown color.

The Rhizobium $F_1$ transconjugant derived from the milky white colonies was cleaned and cultured as described in alternating lines with a strain of *R. trifoli* which was isolated from red clover, found in Randers. The legume extracts used in the medium were derived from the alfalfa, the leaves of *Leucaena leucocephala* and the red clover. The colonies formed by the $F_1$ transconjugant were milky white whereas the colonies formed by *R. trifoli* had a characteristic light brown color.

The Rhizobium F$_2$ transconjugant derived from the snowy white colonies obtained in between the streaks, herein called *Rhizobium oryzae* was cleaned and isolated as described; the F$_2$ transconjugant was used to nodulate rice.

10.2. NODULATION OF RICE WITH RHIZOBIUM ORYZAE

The rice seeds were treated as described by immersion three times in the aqueous solution previously described containing 3% calcium sulphate and up to approximately 10% legume extracts which were used to produce the *R. oryzae*; i.e., the legume extracts used to coat the seeds were derived from the alfalfa, the leaves of *Leucaena leucocephala* and the red clover. After each immersion the seeds were air-dried and sown as described below.

10.2.1. FIELD STUDY

For the Field study, the coated rice seeds were sown as described in Section 6.3.2. The seeds of lot (a) +R−N, were treated as described with a suspension of *R. oryzae* and were watered with non-nitrogenous fertilizer; those of lot (b) −R+N, were not treated with *R. oryzae* but were watered with the inorganic nitrogen fertilizer; and those of lot (c) −R−N, were not treated with either *R. oryzae* or the inorganic nitrogen fertilizer, and were simply watered with the non-nitrogenous fertilizer.

10.3. ANALYSIS OF PROTEIN AND NITROGEN CONTENT OF THE NODULATED RICE

The analytical methods described in Section 6.4. were used to characterize the nodulated rice plants.

10.3.1. RESULTS OF FIELD STUDY

The plants were harvested every 4 ½ months over a 2 ½ year period (2 crops per year) and the protein content per plant was analyzed as previously described.

The results shown in Table V clearly demonstrate that the rice plants treated with *R. oryzae* (+R−N) had a higher protein content than either the group treated with nitrogenous fertilizer (−R−N) or the untreated group (−R−N).

TABLE V

| PROTEIN CONTENT OF RICE | |
|---|---|
| Plant Group | Protein Content per Plant |
| +R−N | 12.0−18% |
| −R+N | 1.5−3% |
| −R−N | 0.5−1% |

11. EXAMPLE: RHIZOBIUM AS A NITROGEN FERTILIZER FOR EUCALYPTUS

A positive effect of Rhizobium as a nitrogen fertilizer was observed with Eucalyptus (family Myrtaceae), a plant species outside the grass family. Of the two species tested, *E. globulus* responded very clearly in increased biomass, however, nodules were not observed.

11.1. PREPARATION OF RHIZOBIUM EU1

*Rhizobium eu1* which has the beneficial effect on Eucalyptus was produced according to the method in Section 6 by first crossing *R. cowpea leucaena* with *R. leguminosarum* to produce the F$_1$ transconjugant which was then crossed with *R. meliloti*. The F$_2$ transconjugant thus produced, *R. eu1*, was used to treat two species of Eucalyptus. This Rhizobium strain does not infect any other plant host described in the examples herein.

11.2. TREATMENT OF EUCALYPTUS WITH RHIZOBIUM EU1

Eucalyptus seeds were pre-germinated, as previously described for cereals, in a legume plant extract of pea, beans, lupin, clover, alfalfa and leucaena. The treated seeds were sown in coarse sand and untreated seeds were sown as a control.

After germination, the pretreated seedlings were watered with non-nitrogenous fertilizer and a suspension of one of six different Rhizobium F$_2$ transconjugants (+R−N). After germination, one group of untreated seedlings was watered with a nitrogenous fertilizer (−R+N) and another group received non-nitrogenous fertilizer (−R−N). Four weeks later the seedlings treated with five of the six Rhizobia strains had all died; however, those treated with *Rhizobium eu1* survived. The surviving plants were transferred individually to six liter pots with soil and a top layer of "Fibo"-clinkers to retain moisture in the pot and prevent growth of fungi. The bottom of the pots were perforated so that excess water could run out, but the amount of non-nitrogenous fertilizer given was adjusted so that no standing water or bacterial contamination was possible. There were 28 pots in all; 14 were +R−N and 14 were −R+N. The 14 +R−N were re-inoculated with *Rhizobium eu1*.

After 4 months growth, the +R−N eucalyptus plants had 2 to 3 times as much biomass as the −R+N plants. Examination of one +R−N plant did not reveal nodules; however, the detection of small nodules is very difficult when the roots grow in soil because soil particles adhere to the roots and discolor the fine roots. Despite the inability to detect nodules in this +R−N Eucalyptus plant, the results indicate that the increased biomass is due to rhizobial nitrogen fixation.

12. EXAMPLE: RHIZOBIUM R1 WHICH NODULATES BRASSICAS

A member of the Brassicas, another plant outside the grass family, also responded positively to Rhizobium treatment. Treatment of rape (*Brassica napus*) with *Rhizobium R1* resulted in plant growth and the appearance of nodules.

12.1. PREPARATION OF RHIZOBIUM R1

*Rhizobium R1* which nodulates rape, was produced according to the method described in Section 6 by first crossing *R. phaseoli* with *R. cowpea leucaena* to produce the F$_1$ transconjugant which was then crossed with *R. trifoli*.

12.2. TREATMENT OF RAPE WITH RHIZOBIUM R1

The rape seeds were pregerminated, as previously described for cereals, in a legume plant extract of bean, leucaena, and clover. The treated seeds were sown in two liter containers and after germination one group was fertilized normally (−R+N), another group was watered with non-nitrogenous fertilizer only (−R−N) and a third group which was also watered with non-nitrogenous fertilizer, was treated with six different strains of Rhizobia (+R−N). After 3 ½ months the −R−N plants still only had the three first juvenile leaves and the +R−N plants treated with three Rhizobia strains designated R4, R5 and R6 were just as poor. However, one of the Rhizobia transconjugants, namely strain R1, was beneficial. The plant treated with Rhizobium R1 had almost the same size and pods as the largest −R+N plant, and small root nodules were visible.

13. EXAMPLE: TOTAL NITROGEN ANALYSIS OF NODULATED NON-LEGUMES

To demonstrate that the nodules elicited by the Rhizobia transformants of the invention in non-legumes were active in nitrogen fixation, Kjeldahl analyses of plant organic nitrogen contents were made.

13.1 MATERIALS AND METHODS

Each of the non-legumes tested were divided into three groups: (a) one was treated with the Rhizobium transconjugant and a non-nitrogenous fertilizer (+R−N); (b) the second group was treated with nitrogenous fertilizer without the Rhizobium transconjugant (−R+N); and (c) the third group was treated with neither the Rhizobium transconjugant nor the nitrogenous fertilizer (−R−N). These group were grown under otherwise identical conditions in the growth house and harvested a number of times throughout the growing period until seeds were mature. Three to five plants were grown in each container and at harvest their shoots were combined. One sample was taken from this material and analyzed for total organic nitrogen. The results presented in the subsections below demonstrate that the nodulated non-legume plants were able to fix nitrogen.

13.2. WHEAT AND BARLEY PLANTS

Two varieties of wheat, Cornette and Ralle, were nodulated using *Rhizobium tritici* as described previously in Section 7. The nitrogen content, expressed as mg nitrogen per plant top and the dry weight of the plant top were assayed. Results are presented in Table VI, below.

TABLE VI

| | | N CONTENT AND DRY WEIGHT OF NODULATED WHEAT | | |
|---|---|---|---|---|
| Days | mg/Plant* | +R−N (n = 4) | −R+N (n = 2) | −R−N (n = 2) |
| | | TRIAL ONE | | |
| 30 | DW | 56.05 ± 28.5 | 90.89 ± 26.3 | 39.69 ± 6.3 |
| | N | 1.14 ± 0.5 | 2.67 ± 0.6 | 0.51 ± 0 |
| 50 | DW | 120.49 ± 27.8 | 257.56 ± 62.3 | 82.61 ± 13.6 |
| | N | 2.26 ± 0.3 | 3.99 ± 1.4 | 0.66 ± 0.3 |
| 64 | DW | 244.78 ± 21.8 | 331.99 ± 5.8 | 72.21 ± 8.7 |
| | N | 3.03 ± 0.3 | 5.01 ± 0.4 | 0.44 ± 0.1 |
| 76 | DW | 314.38 ± 112.5 | 400.64 ± 83.2 | 117.53 ± 44.6 |
| | N | 4.28 ± 1.3 | 6.56 ± 2.1 | 0.69 ± 0.2 |
| 97 | DW | 431.47 ± 68.5 | 666.71 ± 60.3 | 117.0 ± 54.2 |
| | N | 5.19 ± 0.7 | 7.52 ± 1.4 | 0.6 ± 0.2 |
| 115 | DW | 523.49 ± 38.6 | 668.55 ± 113.4 | 82.96 ± 3.2 |
| | N | 5.98 ± 1.2 | 9.94 ± 3.5 | 0.42 ± 0.1 |
| 124 | DW | 565.11 ± 23.2 | 700.77 ± 79.4 | 113.94 ± 12.3 |
| | N | 8.15 ± 0.4 | 11.43 ± 1.9 | 0.67 ± 0 |
| | | TRIAL TWO | | |
| 54 | DW | 158.85 ± 36.3 | 304.91 ± 72.3 | 90.30 ± 12.4 |
| | N | 3.59 ± 0.5 | 7.46 ± 0.8 | 0.51 ± 0.1 |
| 71 | DW | 447.88 ± 83.1 | 705.64 ± 37.0 | 89.54 ± 23.0 |
| | N | 6.28 ± 1.2 | 12.48 ± 1.9 | 0.54 ± 0.2 |
| 80 | DW | 513.37 ± 120.7 | 871.57 ± 205.5 | 117.04 ± 2.6 |
| | N | 7.61 ± 1.1 | 12.15 ± 2.4 | 0.71 ± 0.1 |
| 92 | DW | 903.53 ± 25.6 | 1128.85 ± 166.4 | 131.18 ± 11.8 |
| | N | 11.81 ± 0.45 | 14.56 ± 1.89 | 0.72 ± 0.1 |

*DW = Dry Weight
Plants in Trial One were grown under suboptimal lighting conditions.

The results presented in Table VI indicate that the dry weight of the +R−N plants is about 82% that of the −R+N plants and that the nitrogen content of the +R ™ N plants is about 80% of the −R+N plants.

Five varieties of barley, Jenny, Taarn, Lina, Grith and Triumph, were nodulated using *Rhizobium hordei* as described previously in Section 8. The nitrogen content, expressed as mg nitrogen per plant top and the dry weight of the plant top were assayed. Results are presented in Table VII, below.

TABLE VII

| | | N CONTENT AND DRY WEIGHT OF NODULATED BARLEY | | |
|---|---|---|---|---|
| Days | mg/Plant* | +R−N (n = 10) | −R+N (n = 5) | −R−N (n = 5) |
| | | TRIAL ONE | | |
| 31 | DW | 43.85 ± 9.2 | 71.84 ± 21.7 | 19.15 ± 5.2 |
| | N | 0.99 ± 0.2 | 2.15 ± 0.9 | 0.27 ± 0.1 |
| 50 | DW | 121.53 ± 28.7 | 224.95 ± 44.5 | 35.40 ± 4.2 |
| | N | 2.56 ± 0.5 | 4.03 ± 1.3 | 0.41 ± 0.1 |
| 64 | DW | 198.41 ± 50.7 | 269.92 ± 26.8 | 41.87 ± 7.1 |
| | N | 2.61 ± 0.5 | 4.05 ± 1.1 | 0.35 ± 0.1 |
| 76 | DW | 301.04 ± 56.1 | 296.76 ± 76.9 | 49.58 ± 4.8 |
| | N | 4.09 ± 0.6 | 5.22 ± 2.9 | 0.61 ± 0.3 |
| 96 | DW | 499.23 ± 106.9 | 506.33 ± 106.5 | 55.19 ± 15.7 |
| | N | 5.34 ± 1.4 | 9.90 ± 1.2 | 0.35 ± 0.1 |
| 123 | DW | 535.47 ± 123.7 | 556.38 ± 124.3 | 64.10 ± 11.5 |
| | | 5.55 ± 1.1 | 10.34 ± 3.7 | 0.44 ± 0.1 |
| | | TRIAL TWO | | |
| 54 | DW | 118.89 ± 20.6 | 264.84 ± 38.4 | 49.76 ± 11.8 |
| | N | 3.30 ± 0.4 | 7.78 ± 0.7 | 0.45 ± 0.1 |
| 71 | DW | 313.06 ± 46.1 | 405.53 ± 120.8 | 53.49 ± 9.9 |
| | N | 5.81 ± 0.6 | .78 ± 0.8 | 0.41 ± 0.1 |
| 80 | DW | 711.29 ± 279.6 | 617.75 ± 94.3 | 68.42 ± 2.6 |
| | N | 7.85 ± 1.2 | 10.26 ± 2.4 | 0.53 ± 0.1 |
| 92 | DW | 802.30 ± 147.3 | 837.08 ± 196.4 | 57.07 ± 19.5 |
| | N | 10.08 ± 1.6 | 11.99 ± 1.6 | 0.46 ± 0.2 |

*DW = Dry Weight.

The barley plants nodulated with Rhizobium grow to the same size and dry weight as the plants treated with normal nitrogenous fertilizer. The nitrogen content of the +R−N barley is about 83% that of the −R+N plants, and is 20 times the nitrogen content of the −R−N plants. The nitrogen assayed in the −R−N plants is derived from the seed and does not increase during the growth period.

Notably, the effect of the Rhizobium transconjugants as a substitute for nitrogen fertilizer is due to the action of small nodules which were present on 75% of the plants. Because 3 to 5 plants were grown per container, it was not possible to separate the roots and analyze only the nodulated plants. It is contemplated that nodulation of 100% of the plants and the development of large nodules will function even more effectively.

To eliminate the possibility that the +R−N nodulated non-leguminous plants may use the Rhizobia inoculum or bacteria that may later proliferate in the containers as a source of nitrogen, the following experiment was performed: the Cornette variety of wheat and the Taarn variety of barley were each inoculated with *R. leguminosarum* strain MA1 using the same procedures, amounts and conditions described for inoculating these nonlegume plants with the Rhizobium transconjugant, R. tritici or R. hordei, respectively. The plants inoculated with R. leguminosarum were watered with non-nitrogenous fertilizer and the accumulation of nitrogen was compared to that of −R−N plants. Neither the plants inoculated with R. leguminosarum nor the −R−N plants accumulated nitrogen. The conclusion drawn is that a nonspecific bacterial inoculum, as such, does not supply nitrogen fertilizer to the plants. By contrast, the nitrogen accumulation shown in Tables VII and VIII which occurs in response to nodulation with R. tritici or R. hordei, respectively, must be due to nitrogen fixation.

13.3. SORGHUM AND RICE PLANTS

Three varieties of sorghum, Dabar, Safra and Feterita were nodulated using *Rhizobium sorghi* as described previously in Section 9. The nitrogen content, expressed as mg nitrogen per plant top and the dry weight of the plant top were assayed. Results are presented in Table VIII below.

TABLE VIII

N CONTENT AND DRY WEIGHT OF NODULATED SORGHUM

| Days | mg/Plant* | +R−N (n = 6) | −R+N (n = 3) | −R−N (n = 3) |
|---|---|---|---|---|
| 30 | DW | 38.83 ± 10.1 | 49.60 ± 22.5 | 25.60 ± 4.2 |
|    | N  | 0.40 ± 0.1   | 1.42 ± 0.7   | 0.26 ± 0 |
| 59 | DW | 102.93 ± 15.2 | 329.51 ± 87.7 | 42.84 ± 8.0 |
|    | N  | 1.00 ± 0.2 | 5.93 ± 2.3 | 0.31 ± 0 |
| 80 | DW | 179.84 ± 62.2 | 602.34 ± 44.9 | 43.77 ± 21.5 |
|    | N  | 2.00 ± 0.8 | 9.86 ± 2.7 | 0.31 ± 0 |
| 101 | DW | 439.83 ± 95.8 | 576.18 ± 75.4 | 53.71 ± 12.4 |
|     | N  | 4.40 ± 0.9 | 11.02 ± 0.9 | 0.31 ± 0 |
| 125 | DW | 1242.94 ± 391.4 | 1198.99 ± 596.0 | 56.76 ± 7.8 |
|     | N  | 11.65 ± 2.4 | 12.44 ± 6.8 | 0.27 ± 0 |

*DW = Dry Weight

An M-201 strain of rice was nodulated using *Rhizobium oryzae* as described previously in Section 10. The nitrogen content expressed as mg nitrogen per plant top and the dry weight of the plant top were assayed. Results are presented in Table IX below.

TABLE IX

N CONTENT AND DRY WEIGHT OF NODULATED BARLEY

| Days | mg/Plant* | +R−N | −R+N | −R−N |
|---|---|---|---|---|
| 62 | DW | 32.28 | 48.87 | 23.44 |
|    | N  | 0.32 | 1.10 | 0.16 |
| 74 | DW | 48.04 | 94.73 | 21.63 |
|    | N  | 1.15 | 2.65 | 0.16 |
| 98 | DW | 107.47 | 115.40 | 29.9 |
|    | N  | 2.91 | 3.45 | 0.36 |
| 128 | DW | 174.89 | 130.83 | 22.16 |
|     | N  | 5.16 | 4.33 | 0.38 |

*DW = Dry Weight

The results indicate that the dry weight accumulation of the +R−N plants initially lags behind that of the −R+N plants; however, by the end of the experimental period, the dry matter accumulated by the +R−N plants equals, and may exceed that of the −R+N plans. The accumulation of nitrogen in the +R−N plants and the −R+N plants appears to be about the same.

13.4. RAPE

Two varieties of rape, Hanna and Topas, were nodulated using *Rhizobium Rl* as described previously in Section 12. The nitrogen content, expressed as mg nitrogen per plant top and the dry weight of the plant top were assayed. Results are presented in Table X below.

TABLE X

N CONTENT AND DRY WEIGHT OF NODULATED BARLEY

| Days | mg/Plant* | +R−N | −R+N | −R−N |
|---|---|---|---|---|
| 47 | DW | 67.25 ± 17.4 | 344.91 ± 31.6 | 9.71 ± 0.2 |
|    | N  | 0.89 ± 0.3 | 6.71 ± 0.1 | 0.22 ± 0.2 |
| 59 | DW | 99.40 ± 14.3 | 477.07 ± 62.8 | 13.90 ± 4.5 |
|    | N  | 1.64 ± 0.4 | 7.03 ± 0.2 | 0.11 ± 0.1 |
| 73 | DW | 248.56 ± 24.3 | 766.47 ± 72.7 | 14.92 ± 9.9 |
|    | N  | 2.00 ± 0.7 | 10.25 ± 1.9 | 0.10 ± 0.04 |
| 98 | DW | 424.80 ± 72.5 | 704.74 ± | 12.11 ± 7.9 |
|    | N  | 3.42 ± 1.1 | 17.66 ± 5.1 | 0.10 ± 0.05 |
| 110 | DW | 547.37 ± 22.2 | 1049.77 ± 388.6 | 17.86 ± 12.1 |
|     | N  | 5.73 ± 1.9 | 24.33 ± 7.9 | 0.26 ± 0.2 |
| 129 | DW | 1013.59 ± 241.8 | 1955.60 ± 330.0 | 15.39 ± 6.0 |
|     | N  | 10.24 ± 0.9 | 33.21 ± 8.6 | 0.16 ± 0.09 |
| 147 | DW | 2231.55 | ND | ND |
|     | N  | 16.66 | ND | ND |

*DW = Dry Weight
n = 4 samples
ND = no data.

The results indicate that the +R−N plants accumulated about 50% of the dry weight accumulated by the −R+N plants and the nitrogen content of the +R−N plants was about 30% that of the =R+N plants. Although the accumulation was lower than that of the nitrogen fertilized plants, the small nodules observed in the rape plant account for the survival of the nodulated rape plants grown in the absence of nitrogenous fertilizer (compare results for +R−N to those for −R−N in which neither dry weight nor nitrogen was accumulated).

14. DEPOSIT OF MICROORGANISMS

The following Rhizobium strains have been deposited with the American Type Culture Collection (ATCC), Rockville, Md. and have been assigned the following accession numbers:

| Rhizobium | Accession No. |
|---|---|
| R. tritici | 53,407 |
| R. hordei | 53,404 |
| R. sorghi | 53,405 |
| R. oryzae | 53,406 |
| R. Rl | 53,563 |
| R. eul | 53,562 |

The present invention is not to be limited in scope by the microorganisms deposited since the deposited embodiment is intended as a single illustration of one aspect of the invention and any microorganisms which are functionally equivalent are within the scope of this invention. Indeed, various modifications of the invention in addition to those shown and described herein will become apparent to those skilled in the art from the foregoing description and accompanying figures Such modifications are intended to fall within the scope of the appended claims.

What is claimed is:

1. A Rhizobium transconjugant which fixes nitrogen in wheat plants as deposited with the ATCC and assigned accession number 53,407.

2. A Rhizobium transconjugant which fixes nitrogen in barley plants as deposited with the ATCC and assigned accession number 53,404.

3. A Rhizobium transconjugant which fixes nitrogen in sorghum plants as deposited with the ATCC and assigned accession number 53,405.

4. A Rhizobium transconjugant which fixes nitrogen in rice plants as deposited with the ATCC and assigned accession number 53,406.

5. A Rhizobium transconjugant which fixes nitrogen in Brassica plants as deposited with the ATCC and assigned accession number 53,564.

6. A Rhizobium transconjugant which fixes nitrogen in the vicinity of eucalyptus roots as deposited with the ATCC and assigned accession number 53,562.

7. The Rhizobium transconjugant of claim 1, 2, 3, 4, 5, or 6 characterized a forming snowy white colonies before entering symbiosis with a non-legume host partner when the transconjugant is cultured on a nutrient medium containing, in addition to nutrients required for growth, an extract of each legume host partner of each parent Rhizobium species of the Rhizobium transconjugant.

8. The Rhizobium transconjugant of claim 1, 2, 3, 4, 5, or 6 characterized a forming grey colonies after entering symbiosis with a non-legume host partner when the transconjugant is cultured on a nutrient medium containing, in addition to nutrients required for growth, an extract of each legume host partner of each parent Rhizobium species of the Rhizobium transconjugant and an extract of the non-legume host partner of the Rhizobium transconjugant.

9. The Rhizobium transconjugant of claim 2 which symbiotically fixes nitrogen in the barley strain Hasso.

10. The Rhizobium transconjugant of claim 2 which symbiotically fixes nitrogen in the barley strain Cerise.

11. The Rhizobium transconjugant of claim 2 which symbiotically fixes nitrogen in the barley strain Harry.

12. The Rhizobium transconjugant of claim 2 which symbiotically fixes nitrogen in the barley strain Igri.

13. The Rhizobium transconjugant of claim 6 which is capable of acting as a nitrogen fertilizer for a non-legume belonging to the family Myrtaceae.

14. The Rhizobium transconjugant of claim 13 which is capable of acting as a nitrogen fertilizer for Eucalyptus.

15. A method for producing the Rhizobia $F_2$ transconjugants of claim 1, 2, 3, 4, 5, or 6 that symbiotically fix nitrogen in non-legumes, comprising:
(a) streaking a first Rhizobium parent and a second Rhizobium patent in alternating rows on a solid nutrient medium containing in addition to nutrient essential for growth, a non-denatured shoot extract of a legume host partner of each parent Rhizobium;
(b) culturing the Rhizobia parents at a temperature of about 18° C. to about 30° C. so that the Rhizobia parents form colonies having a specific color;
(c) selecting a Rhizobium $F_1$ transconjugant milky-white colony that grows in between the Rhizobia parent colonies;
(d) streaking the Rhizobium $F_1$ transconjugant in alternating rows with a third Rhizobium parent on the nutrient medium of step (a) further comprising a legume shoot extract of a legume host partner of the third Rhizobia parent;
(e) culturing the Rhizobium $F_1$ transconjugant and the third Rhizobium parent at a temperature of about 18° C. to about 30° C. so that the Rhizobia form colonies; and
(f) selecting a Rhizobium $F_2$ transconjugant snowy white colony that grows in between the Rhizobia $F_1$ transconjugant and the third Rhizobia parent.

16. The method according to claim 15 in which the third Rhizobia parent comprises a third Rhizobia species, a second Rhizobia $F_1$ transconjugant or a second Rhizobia $F_2$ transconjugant.

* * * * *